United States Patent [19]

Chang et al.

[11] Patent Number: 5,741,811
[45] Date of Patent: *Apr. 21, 1998

[54] POLYTHIOPHENE ANTI-TUMOR AGENTS

[75] Inventors: Ching Te Chang, Taipei, Taiwan; Ching-Jer Chang, West Lafayette, Ind.; Chen-Tao Lee, Hsinchu, Taiwan; Fen-Lan Lin, Hsinchu, Taiwan; Jih-Dar Tsai, Hsinchu, Taiwan; Curtis L. Ashendel, West Lafayette, Ind.; Thomas C. K. Chan, Hopkinton, Mass.; Robert L. Geahlen; David J. Waters, both of West Lafayette, Ind.

[73] Assignees: Purdue Research Foundation, W. Lafayette, Ind.; Industrial Technology Research Institute, Hsinchu, Taiwan

[*] Notice: The term of this patent shall not extend beyond the expiration date of Pat. No. 5,578,636.

[21] Appl. No.: 712,854

[22] Filed: Sep. 12, 1996

Related U.S. Application Data

[63] Continuation of Ser. No. 224,828, Apr. 8, 1994, Pat. No. 5,578,636.

[51] Int. Cl.$^6$ .................. A61K 31/38; C07D 409/02
[52] U.S. Cl. .................................... 514/444; 549/59
[58] Field of Search ........................... 549/59; 514/444

[56] References Cited

U.S. PATENT DOCUMENTS

| | | | |
|---|---|---|---|
| 3,050,442 | 8/1962 | Bijloo et al. | 549/59 |
| 4,861,692 | 8/1989 | Kuroda et al. | 549/57 |
| 4,937,256 | 6/1990 | Kober et al. | 544/59 |
| 4,939,165 | 7/1990 | Burkart et al. | 549/59 |
| 5,045,563 | 9/1991 | Morand et al. | 514/444 |
| 5,252,191 | 10/1993 | Pauli et al. | 204/157.67 |
| 5,508,440 | 4/1996 | Chang et al. | 549/59 |
| 5,578,636 | 11/1996 | Chang et al. | 514/444 |
| 5,596,014 | 1/1997 | Chang et al. | 514/444 |

FOREIGN PATENT DOCUMENTS

| | | |
|---|---|---|
| 0344660 A1 | 6/1989 | European Pat. Off. |
| 217985 | 12/1993 | Taiwan . |
| 218379 | 1/1994 | Taiwan . |

OTHER PUBLICATIONS

Abstract, Japanese Patent No. 63,158,555, 01 Jul. 1988.
Abstract, Japanese Patent No. 63,158,557, 01 Jul. 1988.
Abstract, Japanese Patent No. 63,158,558, 01 Jul. 1988.
Abstract, Japanese Patent No. 63,183,448, 28 Jul. 1988.
Abstract, Japanese Patent No. 63,177,143, 21 Jul. 1988.
Abstract, Japanese Patent No. 63,163,368, 06 Jul. 1988.
Abstract of Rossi, Renzo; Carpita, Adriano; Ciofalo, Maurizio; Houben, Julien L.; Synthesis and characterization of 2,2':5,2"-terthiophene derivatives of possible therapeutic use. *Gazz. Chim. Ital.*, 1990, 120(12), pp. 793-803.

Hudson, J.B.; Graham, E.A.; Miki, N.; Towers, G.H.N.; Hudson, L.L.; Rossi, R.; Carpita, A.; Neri, D. Photoactive Antiviral and Cytotoxic Activities of Synthetic Thiophenes and Their Acetylenic Derivatives. *Chemosphere*, vol. 19, Nos. 8/9, pp. 1329-1343, 1989 (I).

Hudson, J.B.; Harris, L.; Teeple, A.; Towers, G.H.N.; The Anti-HIV Activity of the Phytochemical α-Terthienyl, *Antiviral Research*, 20 (1993), pp. 33-43 (II).

Kagan, J.; Naturally Occurring Di-and Trithiophenes, *Prog. Chem. Org. Nat. Prod.*, vol. 56, 1991.

Marles, Robin J.; Arnason, J. Thor; Compadre, R. Lilia; Compadre, Cesar M.; Soucy-Breau, Chantal; Mehta, Bella; Morand, Peter; Redmond, Robert W.; Scaiano, J.C.; Quantitative Structure-Activity Relationship Analysis of Natural Products: Phototoxic Thiophenes, *Modern Phytochemical Methods*, Chapter 11, pp. 371-396, 1991 (I).

Marles, Robin J.; Compadre, R. Lilia; Compadre, Cesar M.; Soucy-Breau, Chantal; Redmond, Robert W.; Duval, France; Mehta, Bella; Morand, Peter; Scaiano, J.C.; Arnason, J. Thor; Thiophenes as Mosquito Larvicides: Structure-Toxicity Relationship Analysis, *Pesticide Biochemistry and Physiology*, vol. 41, pp. 89-100, 1991 (II).

Marles, Robin J.; Hudson, James B.; Graham, Elizabeth A.; Soucy-Breau, Chantal; Morand, Peter; Compadre, R. Lilia; Compadre, Cesar M.; Towers, G.H. Neil; Arnason, J. Thor; Structure-Activity Studies of Photoactivated Antiviral and Cytotoxic Tricyclic Thiophenes, *Photochemistry and Photobiology*, vol. 56, No. 4, pp. 479-487, 1992 III.

MacEachern et al. "Synthesis and Characterization of Alkyl-, Halo- and Hetero-Substituted Derivatives of the Potent Phototoxin α-Terthienyl", Tetrahedron, vol. 44, No. 9 pp. 2403-2412 (1988).

*Primary Examiner*—Deborah Lambkin
*Attorney, Agent, or Firm*—Fish & Richardson P.C.

[57] ABSTRACT

Novel polythiophene compounds useful as anti-tumor agents are described. Preferred compounds of the formula:

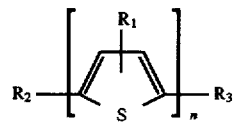

wherein n is 0–2 and $R_2$ and $R_3$ are optionally substituted 2-thienyl or 3-thienyl have been found to exhibit selective cytotoxic activity against transformed human cells. Pharmaceutical compositions containing the described polythiophene compounds are expected to exhibit good chemotherapeutic activity against slow growing tumors based on tumor cell line assays. A method for treating patients having tumors utilizing the disclosed polythiophene compounds is also described.

19 Claims, No Drawings

POLYTHIOPHENE ANTI-TUMOR AGENTS

This is a continuation of application Ser. No. 08/224,828, filed Apr. 8, 1994, U.S. Pat. No. 5,578,636.

GOVERNMENT RIGHTS

This invention was made with Government support under Grant No. 5 UO1 CA50743-02, awarded by the National Cancer Institute. The government has certain rights in the invention.

FIELD OF THE INVENTION

The present invention relates to compositions and a method for treating a patient having a tumor. More specifically, the present invention relates to the treatment of such patients with an effective amount of a polythiophene derivative.

BACKGROUND AND SUMMARY OF THE INVENTION

The control and cure of cancer represents one of our most challenging health problems. The treatment of cancer can be approached by several modes of therapy including surgery, radiation, chemotherapy or a combination of any of these treatments. Chemotherapy continues to be an indispensable therapy for inoperable or metastatic forms of the disease.

The selection of natural compounds, or the synthesis of new compounds having effective anticancer activity is complicated by the still limited knowledge of cancer cell biology and biochemistry. Therefore, development of new effective anti-tumor agents will remain heavily dependent on screening compounds to discover novel compounds having cytotoxic activity. Preferably, such compounds exhibit enhanced cytotoxicity against tumor cells relative to their cytotoxicity to normal cells.

Natural products have a history of providing novel, clinically useful anticancer drugs. Many active natural products have also served as prototypes for the development of new analogs of clinical and preclinical importance. Some specific examples are the Vinca alkaloids (vincristine, vinblastine, vindesine and vinorelbine), podophyllotoxins etoposide and teniposide), taxanes (taxol, taxotere), camptothecins (10-hydroxycamptothecin, 9-dimethylaminomethylcamptothecin, 9-aminocamptothecin and CPT-11), homoharringtonine, adriamycin, daunomycin, bleomycin, mitomycin, idamycin, plicamycin and dactinomycin. It is clear that natural products will continue to be important sources of novel anticancer agents. However, key to the success of novel antitumor drug development programs is the initial identification of potential antitumor agents.

The mouse L1210 leukemia cell line was initially the preferred model system used for screening natural compounds for antitumor activity. However, the P388 murine leukemia system was found to be more sensitive and predictive than L1210 leukemia system, and has been used as primary screen during the past decade. Systematic screening for compounds exhibiting toxicity to these two leukemia cell lines has resulted in the isolation of a large number of active natural products. However, the anticancer activities of these compounds were predominantly in leukemia, lymphoma and a few rare tumors. Low clinical efficacy, or the lack of clinical efficacy of known chemotherapeutics against slower growing solid tumors, is a serious concern.

It has been recognized that the use of a single antileukemia screening system could bias the end results and lead to the isolation of compounds only active in the treatment of fast growing tumors. In addition, the use of a single anti-leukemia screening system may not detect novel compounds with high specificities for particular cell lines. It is also likely that many novel compounds with possible anti tumor activity have remained undetected by the less sensitive in vivo models due to the low concentrations at which many active natural products occur.

Considering the diversity of tumors in terms of cell type, morphology, growth rate and other cellular characteristics, the U.S. National Cancer Institute (NCI) has developed a "disease-oriented" approach to antitumor activity screening (M. R. Boyd, in "Principle of Practice of Oncology" J. T. Devita, S. Hellman, S. A. Rosenberg (Eds.) Vol. 3, PPO Update, No. 10, 1989). This in vitro prescreening system is based on the measurement of antitumor cytotoxicity against human tumor cell line panels consisting of approximately 60 cell lines of major human tumors (including leukemia and slower growing tumor cells such as lung, colon, breast, skin, kidney, etc.). The most important advantage of the new in vitro screening panels is the opportunity to identify compounds that are selectively more cytotoxic to cells of slowly growing solid tumors than to rapidly growing leukemia cells.

Thiophenes are sulfur containing heterocyclic compounds that are distributed widely among the species of the Asteraceae (Compositaie) family, including many species with known medicinal uses. The natural thiophene compounds are thought to play an important role in the chemical defense of plants against herbivorous insects and other pests. Natural thiophenes have been previously described as having cytotoxic activities upon exposure to long wavelength ultraviolet light. Photochemical studies suggest that thiophene phytotoxicity is based primarily on the production of toxic singlet oxygen by a type II photodynamic process. However, polythiophene compounds also exhibit cytotoxic activity in the absence of light activation. More particularly, we have demonstrated that the polythiophene derivatives of the present invention are effective antitumor agents.

In accordance with this invention there is provided a method for the treatment of cancer which utilizes polythiophene compounds of the general formula

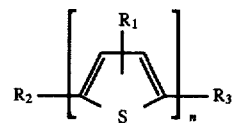

wherein n is 0, 1 or 2, R is H, CHO, $CH_2OH$ or $CH_2NH_2$, and $R_2$ and $R_3$ are independently optionally substituted 2- or 3-thienyl. Further in accordance with this invention there are provided novel cytotoxic compounds of the above formula and chemotherapeutic pharmaceutical compositions containing said compounds in anti-tumor effective amounts.

Additional objects, features, and advantages of the invention will become apparent to those skilled in the art upon consideration of the following detailed description of preferred embodiments exemplifying the best mode of the invention as presently perceived.

DETAILED DESCRIPTION OF THE INVENTION

The present invention is directed to polythiophene compounds, their pharmaceutical compositions and methods utilizing such compounds/compositions for treating patients having tumors. The polythiophene compounds are effective antitumor agents against slow growing tumors. Generally they have been found to exhibit high selective cytotoxicity for individual tumor cell lines.

The compounds of the present invention are polythiophene compounds of the formula:

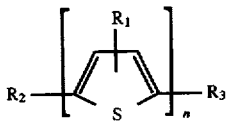

wherein n is 0, 1 or 2, $R_1$ is H, $CH_2OH$, CHO, $CH_2NH_2$, $R_2$ and $R_3$ are independently selected from the group consisting of 2-thienyl, 3-thienyl, mono- or di-substituted 2-thienyl, or mono- or di- substituted 3-thienyl, wherein the thienyl substituents are selected from the group consisting of cyano, chloro, bromo, iodo, $C_1$–$C_7$ alkyl or haloalkyl, $C_1$–$C_7$ alkenyl or haloalkenyl, $C_1$–$C_4$ alkanoyloxy methyl, $CH_2O_4$, $COR_5$, $CH_2NR_6R_7$, $CH(OR_4)R_8$, $CH=CR_9R_{10}$, $CH=NR_{11}$, $CH_2SC(NH)NH_2$ and $C\equiv CR_{12}$ wherein $R_4$ is H, $CO(CH_2)_2CO_2H$, $(CH_2)_2OCH_3$, $C_1$–$C_4$ alkyl, or $COC_11$–$C_{17}$ alkyl;

$R_5$ is H or $C_1$–$C_4$ alkyl;

$R_6$ and $R_7$ are independently H, $C_1$–$C_4$ alkyl, or mono- or di- hydroxy$C_2$–$C_4$ alkyl;

$R_8$ is $C_1$–$C_7$ alkyl, or $C_1$–$C_7$ alkenyl;

$R_9$ and $R_{10}$ are independently H, $C_1$–$C_7$ alkyl, $COOR_5$, $CH(OR_4)COOR_5$, Br, CO-thienyl, $COC_6H_4OH(p)$;

$R_{11}$ is $NHR_4$ or $OR_5$;

$R_{12}$ is $COOR_5$, $CH(OR_5)CH_2OR_5$ or $CH(OCOC_1$–$C_4$ alkyl)$CH_2OR_5$; cyclodextrin complexes of such compound and when $R_2$ or $R_3$ is thienyl substituted with $CH_2NR_6R_7$, the pharmaceutically acceptable salt of the compound represented thereby; with the proviso, that when $R_1$ is H, $R_2$ is selected from the group consisting of 3-thienyl, di- substituted 2-thienyl, hydroxymethyl- or aminomethyl- substituted 2-thienyl, 3-formyl-2-thienyl and mono- or di- substituted 3-thienyl, and $R_3$ is selected from the group consisting of 3-thienyl, di- substituted 2-thienyl, hydroxymethyl- or aminomethyl-substituted 2-thienyl, mono- or di- substituted 3-thienyl and formyl substituted 2-thienyl.

In one preferred embodiment of this invention there is provided anti-tumor polythiophenes of the above formula wherein n is 1, R is H, $R_2$ is 3-thienyl or substituted 3-thienyl and R3 is 2-thienyl or substituted 2-thienyl. Such polythiophene compounds, especially those wherein $R_2$ is 3-thienyl and $R_3$ is 2-thienyl optionally substituted with $CH_2NH_2$, $CH_2OH$ or CHO, exhibit cytotoxic selectivity against transformed human cells.

Other preferred compounds in accordance with this invention are those polythiophenes of the above formula wherein n is 1, $R_1$ is hydrogen, $R_2$ is hydroxymethyl 2-thienyl and $R_3$ is 2-thienyl optionally substituted with $CH_2NH_2$, $CH_2OH$ or CHO.

Still another preferred group of polythiophene compounds of this invention are those of the above formula wherein $R_2$ is optionally substituted 2-thienyl and $R_3$ is 3-or 4-substituted-2-thienyl wherein the substitutes are selected from $CH_2OH$, CHO and $CH_2NH_2$.

Another group of polythiophene compounds within the scope of this invention are compounds of the formula:

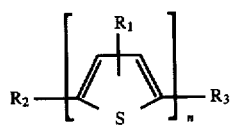

wherein n is 0,1 or 2, $R_1$ is H, $CH_2OH$, CHO, $CH_2NH_2$, $R_2$ is selected from the group consisting of 2-thienyl, 3-thienyl, mono- or di- substituted 2-thienyl, or mono- or di- substituted 3-thienyl, and $R_3$ is selected from the group consisting of 3-thienyl, mono- or di- substituted 3-thienyl and di- substituted 2-thienyl, wherein the thienyl substituents are selected from the group consisting of cyano, chloro, bromo, iodo, $C_1$–$C_7$ alkyl or haloalkyl, $C_1$–$C_7$ alkenyl or haloalkenyl, $C_1$–$C_4$ alkanoyloxy methyl, $CH_2OR_4$, $COR_5$, $CH_2NR_6R_7$, $CH(OR_4)R_8$, $CH=CR_9R_{10}$, $CH=NR_{11}$, $CH_2SC(NH)NH_2$ and $C\equiv CR_{12}$ wherein $R_4$ is H, $CO(CH_2)_2CO_2H$, $(CH_2)_2OCH_3$, $C_1$–$C_4$ alkyl, or $COC_1$–$C_{17}$ alkyl;

$R_5$ is H or $C_1$–$C_7$ alkyl;

$R_6$ and $R_7$ are independently H, $C_1$–$C_4$ alkyl, or mono- or di- hydroxy$C_2$–$C_4$ alkyl;

$R_8$ is $C_1$–$C_7$ alkyl, or $C_1$–$C_7$ alkenyl;

$R_9$ and $R_{10}$ are independently H, $C_1$–$C_4$ alkyl, $COOR_5$, $CH(OR_4)COOR_5$, Br, CO-thienyl, $COC_6H_4OH(p)$;

$R_{11}$ is $NHR_4$ or $OR_5$;

$R_{12}$ is $COOR_5$, $CH(OR_5)CH_2OR_5$ or $CH(OCOC_1$–$C_4$ alkyl)$CH_2OR_5$; cyclodextrin complexes of such compound and when $R_2$ or $R_3$ is thienyl substituted with $CH_2NR_6R_7$, the pharmaceutically acceptable salt of the compound represented thereby.

The polythiophene compounds of this invention are readily formulated into pharmaceutical compositions, also within the scope of this invention, for use in the presently described method for treatment of patients having tumors. In one preferred embodiment of this invention, the pharmaceutical composition comprises an anti-tumor effective amount of a polythiophene compound of the formula:

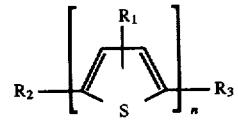

wherein n is 0, 1 or 2, $R_1$ is H, $CH_2OH$, CHO, $CH_2NH_2$, $R_2$ and $R_3$ are independently selected from the group consisting of 2-thienyl, 3-thienyl, mono- or di-substituted 2-thienyl, or mono- or di- substituted 3-thienyl, wherein the thienyl substituents are selected from the group consisting of cyano, chloro, bromo, iodo, $C_1$–$C_7$ alkyl or haloalkyl, $C_1$–$C_7$ alkenyl or haloalkenyl, $C_1$–$C_4$ alkanoyloxy methyl, $CH_2OR_4$, $COR_5$, $CH_2NR_6R_7$, $CH(OR_4)R_8$, $CH=CR_9R_{10}$, $CH=NR_{11}$, $CH_2SC(NH)NH_2$ and $C\equiv CR_{12}$ wherein $R_4$ is H, $CO(CH_2)_2CO_2H$, $(CH_2)_2OCH_3$, or $COC_1$–$C_{17}$ alkyl;

$R_5$ is H or $C_1$–$C_7$ alkyl;

$R_6$ and $R_7$ are independently H, $C_1$–$C_4$ alkyl, or mono- or di- hydroxy$C_2$–$C_4$ alkyl;

$R_8$ is $C_1$–$C_7$ alkyl, or $C_1$–$C_7$ alkenyl;

$R_9$ and $R_{10}$ are independently H, $C_1$–$C_7$ alkyl, $COOR_5$, $CH(OR_4)COOR_5$, Br, CO-thienyl, or $COC_6H_4OH(p)$;

$R_{11}$ is $NHR_4$ or $OR_5$;

$R_{12}$ is $COOR_5$, $CH(OR_5)CH_2OR_5$ or $CH(OCOCC_1$–$C_4$ alkyl)$CH_2OR_5$; cyclodextrin complexes of such compound and when $R_2$ or $R_3$ is thienyl substituted with $CH_2NR_6R_7$, the pharmaceutically acceptable salt of the compound represented thereby; with the proviso, that when $R_1$ is H, $R_2$ is selected from the group consisting of 2-thienyl, 3-thienyl, mono- or di-substituted 2-thienyl, or mono- or di- substituted 3-thienyl, and $R_3$ is selected from the group consisting of 3-thienyl, mono- or di- substituted 2-thienyl, or mono- or di- substituted 3-thienyl, and a pharmaceutically acceptable carrier.

Another pharmaceutical composition within the scope of this invention comprises an anti-tumor effective amount of compound of the formula:

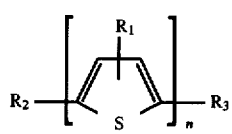

wherein n is 0, 1 or 2, $R_1$ is H, $CH_2OH$, CHO, $CH_2NH_2$, $R_2$ is selected from the group consisting of 2-thienyl, 3-thienyl, mono- or di- substituted 2-thienyl, or mono- or di- substituted 3-thienyl, and $R_3$ is selected from the group consisting of 3-thienyl, mono- or di- substituted 3-thienyl, di- substituted 2-thienyl wherein the thienyl substituents are selected from the group consisting of cyano, chloro, bromo, iodo, $C_1$–$C_7$ alkyl or haloalkyl, $C_1$–$C_7$ alkenyl or haloalkenyl, $C_1$–$C_4$ alkanoyloxy methyl, $CH_2OR_4$, $COR_5$, $CH_2NR_6R_7$, $CH(OR_4)R_8$, $CH=CR_9R_{10}$, $CH=NR_{11}$, $CH_2SC(NH)NH_2$ and $C\equiv CR_{12}$ wherein $R_4$ is H, $CO(CH_2)_2CO_2H$, $(CH_2)_2OCH_3$, $C_1$–$C_4$ alkyl or $COCC_1$–$C_{17}$ alkyl;

$R_5$ is H or $C_1$–$C_7$ alkyl;

$R_6$ and $R_7$ are independently H, $C_1$–$C_4$ alkyl, or mono- or di- hydroxy$C_2$–$C_4$ alkyl;

$R_8$ is $C_1$–$C_7$ alkyl, or $C_1$–$C_7$ alkenyl;

$R_9$ and $R_{10}$ are independently H, $C_1$–$C_7$ alkyl, $COOR_5$, $CH(OR_4)$ $COOR_5$, Br, CO-thienyl, or $COC_6H_4OH(p)$;

$R_{11}$ is $NHR_4$ or $OR_5$;

$R_{12}$ is $COOR_5$, $CH(OR_5)$ $CH_2OR_5$ or $CH(OCOC_1$–$C_4$ alkyl) $CH_2OR_5$; cyclodextrin complexes of such compound and when $R_2$ or $R_3$ is thienyl substituted with $CH_2NR_6R_7$, the pharmaceutically acceptable salt of the compound represented thereby, and a pharmaceutically acceptable carrier.

The present compounds are readily prepared using art-recognized chemical-synthesis procedures as exemplified hereinbelow. The art is replete with descriptions of the chemistry and synthesis of thiophene and polythiophene compounds.

Tables 1, 2, 3 and 4 hereinbelow show several polythiophene compounds that have been tested at the National Cancer Institute. The growth inhibition profiles of several polythiophenes are shown in Tables 5, 6 and 7. The unusually strong activities against solid tumors are predictive of significant therapeutic potency for the treatment of cancer.

TABLE 1

Compounds registered and tested by NCI

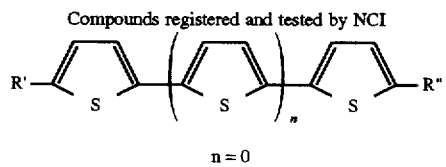

n = 0

| NSC Code | R' | R" |
|---|---|---|
| 645279 | $CH_2OH$ | H |
| 649652 | $CH_2OTs$ | H |
| 203017 | $COCH_3$ | $COCH_3$ |
| 649653 | I | I |
| 649654 | $CH=CBr_2$ | H |
| 649656 | $CH=CHCOTh$ | H |
| 649657 | $CH=CHCOC_6H_4OH(p)$ | H |
| 649658 | $CH_2NHC_6H_5$ | H |
| 649659 | $CH=NCH_2CH(OH)CH_2OH$ | H |
| 647070 | $CH=C(CN)COOH$ | H |
| 645276 | $C\equiv CCH(OH)CH_2OH$ | H |
| 645277 | $C\equiv CCH(OAc)CH_2OH$ | |
| 646271 | $CH=N-OH$ (syn) | H |
| 646655 | $CN=N-OH$ (anti) | H |
| 647073 | CHO | $CH_2OH$ |
| 647074 | CHO | $C_7H_{15}$ |
| 647450 | $CH_2OH$ | $C_7H_{15}$ |
| 647451 | $COC_6H_{13}$ | H |
| 647452 | $CH_2OH$ | $CH_2OH$ |
| 647453 | CHO | $CH_2OAC$ |
| 652869 | $CH_2OCO(CH_2)_2CO_2H$ | CHO |
| 542870 | $CH_2OCO(CH_2)_2CO_2H$ | $CH_2OCO(CH_2)_2CO_2H$ |

THP: tetrahydropyranyl
TS: tosyl
TH: thienyl
Ac: actyl
Et: ethyl

TABLE 2

Compounds registered and tested by NCI

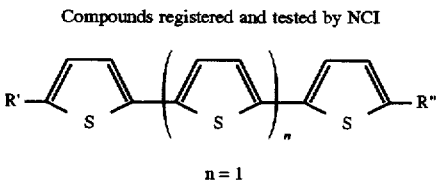

n = 1

| NSC Code | R' | R" |
|---|---|---|
| 637393 | CHO | H |
| 637394 | CHO | CHO |
| 637388 | $CH_2OH$ | H |
| 645278 | $CH_2OAc$ | H |
| 639392 | $CH_2OEt$ | H |
| 659566 | $CH(OH)CH_3$ | H |
| 659567 | $COCH_3$ | H |
| 637389 | CN | H |
| 637390 | CN | CN |
| 637391 | $CH=CHCOOH$ | H |
| 637392 | $CH=C(COOH)_2$ | H |
| 646267 | $CH=NNHC_6H_5$ | H |
| 646268 | $CH=N-OH$ | H |
| 660642 | $CH_2SC(NH_2)=NH$ | H |
| 646269 | $C=CCO_2Et$ | H |
| 646270 | $CH_2OH$ | $CH_2OH$ |
| 646272 | $CH_2O(CH_2)_2OCH_3$ | H |
| 647072 | $CH_2OH$ | $CH_3$ |
| 647454 | $CH_3$ | H |
| 647455 | CHO | $CH_2OH$ |
| 649662 | $COC_2H_5$ | H |
| 649663 | $CH(OH)C_2H_5$ | H |
| 651690 | $CH_2OCO(CH_2)_2CO_2H$ | H |

TABLE 2-continued

Compounds registered and tested by NCI

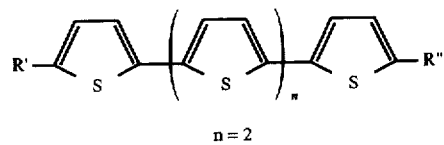

n = 1

| NSC Code | R' | R" |
|---|---|---|
| 652866 | $CH_2NH_2$ | H |
| 660645 | $CH_2NH_3$ tartarate | H |
| 656898 | $CH_2NH_2$ | $CH_2OH$ |
| 658110 | $CH_2NH_2$ | $CH_2NH_2$ |
| 659562 | $CH_2NHCH_3$ | H |
| 658466 | $CH_2NHCH_2CH(OH)CH_2OH$ | H |
| 659563 | $CH_2N(CH_3)_2$ | H |
| 659561 | $CH_2N(C_2H_5)_3Cl$ | H |
| 659564 | $CH_2N(CH_3)_2$ | $CH_2N(CH_3)_2$ |
| 659565 | $CH_2NCCH_3)_2$ | $CH_2OH$ |

TABLE 3

Compounds registered and tested by NCI n = 2

| NSC Code | R' | R" |
|---|---|---|
| 645273 | CHO | H |
| 645274 | $CH_2OH$ | H |

TABLE 4

Compounds registered and tested by NCI

| NSC Code | Structure |
|---|---|
| 663565 | HOH₂C—[thiophene]—[thiophene]—CHO |
| 663565 | HOH₂C—[thiophene]—[thiophene]—CH₂OH |
| 658111 | [thiophene]—[thiophene]—[thiophene]—CHO |
| 658465 | [thiophene]—[thiophene]—[thiophene(CHO)]—[thiophene] |
| 658112 | [thiophene]—[thiophene]—[thiophene]—CH₂OH |
| 658113 | [thiophene]—[thiophene]—[thiophene(CH₂OH)]—[thiophene] |

TABLE 4-continued

Compounds registered and tested by NCI

| NSC Code | Structure |
|---|---|
| 658880 | OHC–[S]–[S]–[S]–CHO |
| 658877 | OHC–[S]–[S]–[S(CHO)] |
| 658879 | OHC–[S]–[S]–[S]–CH$_2$OH |
| 658876 | OHC–[S]–[S]–[S(CH$_2$OH)] |
| 658878 | HOH$_2$C–[S]–[S]–[S]–CH$_2$OH |
| 658875 | HOH$_2$C–[S]–[S]–[S(CH$_2$OH)] |
| 663560 | [S]–[S]–[S]–(CHO)(CHO) |
| 663562 | [S]–[S]–[S]–(CHO)(CH$_2$OH) |
| 663561 | [S]–[S]–[S]–(CH$_2$OH)(CH$_2$OH) |
| 666164 | OHC–[S]–[S(CH$_2$OH)]–[S]–CHO |
| 666165 | HOH$_2$C–[S]–[S(CH$_2$OH)]–[S]–CH$_2$OH |
| 660643 | [S]–[S]–[S]–[S]–CHO (with branching thiophene) |

TABLE 4-continued

Compounds registered and tested by NCI

| NSC Code | Structure |
|---|---|
| 660644 | 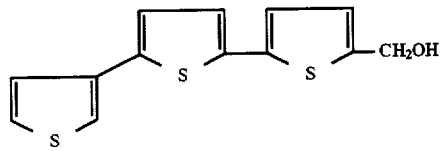 |

TABLE 5

The growth inhibition of the human cancer cell lines by polythiophene
$Log_{10} GI_{50} (M)$

| | Compd. | | | |
|---|---|---|---|---|
| Cell Line | $(\text{thiophene})_2$—CH$_2$OH | $(\text{thiophene})_3$—CH$_2$OH | $(\text{thiophene})_3$—CH$_2$OAc | $(\text{thiophene})_3$—CHO |
| Lung Cancer | | | | |
| A549/ATCC | −5.05 | | −5.18 | −4.49 |
| EKVX | | | −4.61 | −4.26 |
| HOP-18 | −4.98 | −4.65 | −5.63 | |
| HOP-62 | −5.01 | | −4.62 | |
| NCI-H23 | | −4.15 | −4.71 | −4.26 |
| NCI-H226 | −6.50 | −6.93 | −6.49 | −7.61 |
| NCI-H322M | −4.52 | −4.53 | −4.71 | −4.37 |
| NCI-H460 | −5.87 | −6.31 | −5.82 | −4.86 |
| NCI-H522 | −4.02 | | −4.88 | −4.49 |
| LXPL-529 | −6.54 | <−8.00 | <−8.00 | <−8.00 |
| Colon Cancer | | | | |
| COLO-205 | −5.44 | −6.04 | −6.36 | −5.27 |
| DLD-1 | −6.50 | −5.35 | <−8.00 | −5.10 |
| HCC-2998 | | −4.44 | −4.61 | −4.75 |
| HCT-116 | −5.34 | −6.53 | | −7.20 |
| HCT-15 | −4.45 | | −4.30 | −4.62 |
| HT29 | −5.07 | | −4.52 | −4.61 |
| KM20L2 | −5.80 | −6.61 | −6.88 | −6.31 |
| SW-620 | −5.33 | | | −6.27 |
| CNS Cancer | | | | |
| SF-268 | | | −4.61 | −4.06 |
| SF-295 | −4.42 | −4.47 | −4.74 | −4.16 |
| SNB-75 | −6.41 | | <−8.00 | −4.50 |
| SNB-19 | | −4.73 | | |
| U251 | −6.34 | −6.83 | <−8.00 | |
| XF-498 | −5.43 | | | |
| Melanoma | | | | |
| LOX IMVI | | | −4.62 | |
| MALME-3M | | | −4.49 | −4.10 |
| M-14 | | | −4.40 | −4.20 |
| SK-MEL-2 | | | −4.14 | −4.51 |
| SK-MEL-28 | | | | −4.05 |
| UACC-257 | −6.03 | −6.99 | −7.03 | −7.33 |
| UACC-62 | | <−8.00 | −4.77 | −8.00 |
| Ovarian Cancer | | | | |
| IGROV-1 | | −7.37 | −5.30 | −7.22 |
| OVCAR-3 | −5.63 | | −7.59 | −7.52 |
| OVCAR-4 | | | | −4.51 |
| OVCAR-5 | −4.89 | −6.65 | −4.58 | −6.86 |
| OVCAR-8 | −4.28 | | | −4.27 |
| SK-OV-3 | | | −4.04 | −4.06 |
| Renal Cancer | | | | |
| 786-0 | −4.49 | | −4.73 | −4.36 |
| A-498 | | <−8.00 | −7.36 | −7.36 |

TABLE 5-continued

The growth inhibition of the human cancer cell lines by polythiophene
$\text{Log}_{10}\ \text{GI}_{50}$ (M)

| Cell Line | $\left(\underset{S}{\langle\!\!\!\sqrt{\phantom{x}}\rangle}\right)_2$—CH$_2$OH | $\left(\underset{S}{\langle\!\!\!\sqrt{\phantom{x}}\rangle}\right)_3$—CH$_2$OH | $\left(\underset{S}{\langle\!\!\!\sqrt{\phantom{x}}\rangle}\right)_3$—CH$_2$OAc | $\left(\underset{S}{\langle\!\!\!\sqrt{\phantom{x}}\rangle}\right)_3$—CHO |
|---|---|---|---|---|
| ACHN |  |  | −4.75 | −4.29 |
| CAKI-1 | −6.65 | −7.56 | −7.74 | −7.86 |
| RXF-393 | −4.24 | −7.50 | −4.74 | −4.78 |
| RXF-631 | −6.09 | −7.55 | <−8.00 |  |
| SN12C |  |  | −4.54 | −4.32 |
| TK-10 | −6.63 | −6.98 | −6.92 | −6.28 |
| UO-31 | −4.41 |  | −4.73 | −4.38 |

GI$_{50}$: molar concentration required for 50% growth inhibition

TABLE 6

The growth inhibition of the human cancer cell lines by chemically modified a-polythiophene derivatives
$\text{Log}_{10}\ \text{GI}_{50}$ M

| Cell Line | $\left(\underset{S}{\langle\!\!\!\sqrt{\phantom{x}}\rangle}\right)_2$—(CH$_2$OH)$_2$ | $\left(\underset{S}{\langle\!\!\!\sqrt{\phantom{x}}\rangle}\right)_3$—(CH$_2$OH)$_2$ | $\left(\underset{S}{\langle\!\!\!\sqrt{\phantom{x}}\rangle}\right)_3$—(CHO)$_2$ | $\left(\underset{S}{\langle\!\!\!\sqrt{\phantom{x}}\rangle}\right)_4$—CH$_2$OH |
|---|---|---|---|---|
| Lung Cancer | | | | |
| A549/ATCC | −5.91 | | | |
| HOP-18 | −5.51 | | | |
| HOP-62 | −5.52 | | | |
| HOP-92 | −4.09 | | | |
| NCI-H226 | −7.60 | −7.88 | −5.76 | −5.23 |
| NCI-H322M | −5.77 | | | |
| NCI-H460 | −6.29 | −7.80 | −5.62 | |
| LXPL-529 | −6.33 | <−8.00 | −5.95 | −5.98 |
| Colon Cancer | | | | |
| COLO-205 | −6.22 | −6.81 | | |
| DLD-1 | −4.74 | | | |
| HCT-116 | −5.27 | −7.82 | −4.74 | |
| HCT-15 | −4.19 | | | |
| HT29 | −5.04 | | | |
| KM20L2 | −6.15 | −6.84 | −4.39 | |
| KM12 | −4.35 | | | |
| SW-620 | −5.04 | −7.17 | | |
| HCC-2998 | −6.40 | −5.74 | | |
| CNS Cancer | | | | |
| SNB-78 | | −4.44 | | |
| SNB-75 | | −4.43 | −4.14 | |
| SNB-19 | −4.72 | −4.97 | | |
| U251 | | −7.73 | −6.09 | |
| XP-498 | | −7.52 | | −4.96 |
| SF-295 | | −4.43 | | |
| Melanoma | | | | |
| UACC-257 | −6.00 | −7.87 | −5.72 | −4.97 |
| UACC-62 | −6.36 | <−8.00 | −6.46 | |
| Ovarian Cancer | | | | |
| IGROV-1 | −6.57 | <−8.00 | −5.15 | −5.95 |
| OVCAR-3 | −5.70 | <−8.00 | | |
| OVCAR-4 | −4.46 | | | |
| OVCAR-5 | −6.06 | −7.52 | −4.68 | |
| OVCAR-8 | −5.23 | −4.10 | | |
| SK-OV-3 | −5.80 | −5.38 | | |

TABLE 6-continued

The growth inhibition of the human cancer cell lines by chemically modified a-polythiophene derivatives
$Log_{10}\ GI_{50}\ M$

| Cell Line | Compd. | | | |
|---|---|---|---|---|
| | (thiophene)$_2$—(CH$_2$OH)$_2$ | (thiophene)$_3$—(CH$_2$OH)$_2$ | (thiophene)$_3$—(CHO)$_2$ | (thiophene)$_4$—CH$_2$OH |
| Renal Cancer | | | | |
| A-498 | −7.71 | <−8.00 | −5.93 | |
| CAKI-1 | −6.63 | <−8.00 | −5.88 | −6.21 |
| RXF-631 | | <−8.00 | −4.03 | −4.96 |
| TK-10257 | −6.29 | −7.84 | −5.29 | −6.05 |
| RXF-393 | −7.05 | | | |

$GI_{50}$: Concentration required for 50% growth inhibition

TABLE 7

Growth inhibition of the human solid cancer cell lines by polythiophenes
$LOG_{10}\ GI_{50}\ (M)$

| Cell Line | Compd. | |
|---|---|---|
| | (terthiophene branched)—CH$_2$OH | HOH$_2$C—(terthiophene)—CH$_2$OH |
| HOP-62 | −4.69 | |
| HOP-92 | −4.41 | −5.03 |
| NCI-H23 | −4.62 | >5.00 |
| NCI-H226 | | −7.85 |
| NCI-H322M | −4.79 | −5.37 |
| NCI-H460 | −4.60 | −7.41 |
| NCI-H522 | | |
| Colon Cancer | | |
| COLO-205 | −6.04 | −6.72 |
| HCC-2998 | −6.01 | −5.23 |
| HCT-116 | −6.44 | −6.97 |
| HCT-15 | −4.23 | >−5.00 |
| HT29 | −4.86 | −6.63 |
| KM12 | −4.08 | >−5.00 |
| SW-620 | −4.32 | |
| CNS Cancer | | |
| SF-268 | −4.27 | >−5.00 |
| SF-295 | −4.45 | >−5.00 |
| SF-539 | | >−5.00 |
| SNB-19 | −4.48 | >−5.00 |
| SNB-75 | −4.51 | −5.70 |
| U251 | −4.97 | −5.25 |
| Melanoma | | |
| MALME-3M | −4.41 | >−5.00 |
| M14 | −4.37 | >−5.00 |
| SK-MEL-28 | −4.44 | >−5.00 |
| SK-MEL-5 | −4.38 | >−5.00 |
| UACC-257 | −6.72 | −7.42 |
| UACC-62 | | −6.74 |
| LOX1MV1 | | >−5.00 |
| SK-MEL-2 | | >−5.00 |
| Ovarian Cancer | | |
| IGROV1 | −6.66 | −6.84 |
| OVCAR-3 | −6.80 | −7.16 |
| OVCAR-4 | −4.60 | −6.52 |
| OVCAR-5 | −6.38 | −6.90 |

TABLE 7-continued

Growth inhibition of the human solid cancer cell lines by polythiophenes LOG$_{10}$ GI$_{50}$ (M)

| | | |
|---|---|---|
| OVCAR-8 | -4.24 | >-5.00 |
| Renal Cancer | | |
| | | |
| 786-0 | -4.24 | |
| A498 | -6.94 | -7.80 |
| CAKI-1 | -7.64 | -7.60 |
| RXF-393 | -4.69 | >-5.00 |
| TK-10 | -6.69 | -7.10 |
| UO-31 | | |
| SN12C | | |
| ACHN | | >-5.00 |
| Prostate Cancer | | |
| | | |
| PC-3 | -4.29 | >-5.00 |
| DU-145 | -4.18 | >-5.00 |
| Breast Cancer | | |
| | | |
| MCF7 | -6.59 | -6.86 |
| MCF7/ADR-RES | | >-5.00 |
| MDA-MB-231/ATCC | -4.55 | >-5.00 |
| MDA-N | -6.30 | -5.02 |
| T-47D | -6.47 | -6.65 |
| HS 578T | | -5.11 |
| MDA-MB-435 | | -5.36 |
| BT-549 | | >-5.00 |

| Cell Line | Compd. (structure: thiophene dimer with CH$_2$OH groups) | |
|---|---|---|
| HOP-62 | -4.70 | |
| HOP-92 | | |
| NCI-H23 | -4.41 | |
| NCI-H226 | -6.59 | |
| NCI-H322M | | |
| NCI-H460 | -5.25 | |
| NCI-H522 | -4.47 | |
| Colon Cancer | | |
| | | |
| COLO-205 | -5.23 | |
| HCC-2998 | -6.50 | |
| HCT-116 | | |
| HCT-15 | -4.55 | |
| HT29 | -4.73 | |
| KM12 | -4.78 | |
| SW-620 | -4.39 | |
| CNS Cancer | | |
| | | |
| SF-268 | | |
| SF-295 | -4.47 | |
| SF-539 | | |
| SNB-19 | | |
| SNB-75 | | |
| U251 | -4.16 | |
| Melanoma | | |
| | | |
| MALME-3M | -4.53 | |
| M14 | -4.29 | |
| SK-MEL-28 | -4.40 | |
| SK-MEL-5 | >-5.00 | |
| UACC-257 | | |
| UACC-62 | | |
| LOX1MV1 | | |
| SK-MEL-2 | | |
| Ovarian Cancer | | |
| | | |
| IGROV1 | -6.64 | |
| OVCAR-3 | | |

TABLE 7-continued

Growth inhibition of the human solid cancer cell
lines by polythiophenes
$LOG_{10}$ $GI_{50}$ (M)

| | | |
|---|---|---|
| | OVCAR-4 | |
| | OVCAR-5 | |
| | OVCAR-8 | −4.30 |
| | Renal Cancer | |
| | 786-0 | −4.28 |
| | A498 | |
| | CAKI-1 | |
| | RXF-393 | −5.06 |
| | TK-10 | −4.68 |
| | UO-31 | −4.19 |
| | SN12C | −4.33 |
| | ACHN | −4.25 |
| | Prostate Cancer | |
| | PC-3 | −4.31 |
| | DU-145 | −4.26 |
| | Breast Cancer | |
| | MCF7 | −6.75 |
| | MCF7/ADR-RES | −4.24 |
| | MDA-MB-231/ATCC | |
| | MDA-N | −5.27 |
| | T-47D | −6.37 |
| | HS 578T | −4.28 |
| | MDA-MB-435 | −4.82 |
| | BT-549 | −4.08 |

The cytotoxic activity of the present polythiophene compounds have been measured utilizing three different assays or screens. The first screen measures the cytotoxicity against a panel of sixty different human tumor cell lines. This assay provides data regarding the general cytotoxicity of an individual compound. In particular this type of assay is useful in identifying compounds which have enhanced cytotoxic activity against slow growing tumors as compared to faster growing tumor cells such as leukemia tumor cell lines. The identification of such compounds is critical since previously identified antitumor agents have low cytotoxic activity against slower growing tumors. The specificity of a compound for a limited number of tumor cell lines also indicates that such a compound will likely be less cytotoxic to normal cells. The specificity of a cytotoxic compound for tumor cell lines relative to normal cells is an important characteristic of an effective antitumor agent.

Antitumor cytotoxicity data for the National Cancer Institute human tumor cell panels can also be expressed in a graphic pattern (mean graph) to display differential cell growth inhibition (K. D. Paull, R. H. Shoemaker, L. Hodes, A. Monks, D. A. Scudiero, L. Rubinstein, J. Plowman and M. R. Boyd, *J. Natl. Cancer Inst.*, 81, 1088, 1989.) In the mean graph, the arithmetic mean of the logarithm of the $GI_{50}$ (50% growth inhibition), TGI (total growth inhibition) or $LC_{50}$ (50% lethal concentration) values is used as an anchor point. Relative cytotoxicity is displayed by projecting bars to the right or left of the mean, depending on whether cell sensitivity to a test compound is more or less than average. The length of a bar is indicative of differential cytotoxicity against a specific type of tumor cells or tumor panels.

In a second assay, the cytotoxic selectivity is assessed by comparing compound cytotoxicity against transformed cells and normal cells. $IC_{50}$ values were compared between treated TBE cells (ras-transformed human bronchial epithelial cells) and NHBE cells (Normal human bronchial epithelial cells). Cytotoxic effects on normal human bronchial epithelial cells (NMBE) and ras-transformed human bronchial epithelial cells (TBE) were measured by the cell count (cell member) using Coulter Z. F. counter (Hialeah, Fla.) carried out at Purdue University. The result is expressed as $GI_{50}$, concentration of drug at which cell numbers are reduced to 50% of control cell culture (T. C. K. Chan, C.-j. Chang, N. M. Koonchanok and R. L. Geahlen, *Biochem. Biophys. Res. Commun.*, 193, 1152, 1993). The data presented in Table 8 illustrates that polythiophenes generally exhibit greater cytotoxicity for transformed human cells in comparison to the normal human cells.

TABLE 8

Selective cytotoxicity against ras-oncogene transformed human bronchial epithelial cells

| NSC Code | Structure | GI$_{50}$ (µg/ml) TBE | NHBE |
|---|---|---|---|
| 637393 | terthiophene-CHO | 0.03 | 0.2 |
| 637388 | terthiophene-CH$_2$OH | 0.02 | 3.0 |
| 652866 | terthiophene-CH$_2$NH$_2$ | 0.001 | 0.01 |
| 659561 | terthiophene-CH$_2$N(Et)$_3^+$ | 2 | 5 |
| 637394 | OHC-terthiophene-CHO | 0.01 | 0.2 |
| 646270 | HOH$_2$C-terthiophene-CH$_2$OH | 0.02 | 1.0 |
| 647073 | HOH$_2$C-bithiophene-CHO | 0.05 | 0.08 |
| 647452 | HOCH$_2$-bithiophene-CH$_2$OH | 0.03 | 0.6 |
| 647455 | HOH$_2$C-terthiophene-CHO | 0.002 | 0.1 |
| 656898 | HOH$_2$C-terthiophene-CH$_2$NH$_2$ | 0.02 | 3.0 |
| 658110 | H$_2$NH$_2$C-terthiophene-CH$_2$NH$_2$ | 4.0 | 10 |
| 658879 | OHC-terthiophene (3-CH$_2$OH) | 0.004 | 6.2 |
| 658878 | HOH$_2$C-terthiophene (3-CH$_2$OH) | 0.002 | 8.0 |
| 658877 | OHC-terthiophene (3-CHO) | 0.03 | 0.6 |
| 658876 | OHC-terthiophene (3-CH$_2$OH) | 0.02 | 0.4 |

TABLE 8-continued

Selective cytotoxicity against ras-oncogene transformed human bronchial epithelial cells

| NSC Code | Structure | GI$_{50}$ (μg/ml) | |
|---|---|---|---|
| | | TBE | NHBE |
| 658875 | HOH$_2$C–[thiophene]–[thiophene]–[thiophene]–CH$_2$OH | 0.002 | 9.7 |
| 660643 | [thiophene]–[thiophene]–[thiophene]–CHO (with pendant thiophene) | 0.005 | 2.4 |
| 660644 | [thiophene]–[thiophene]–[thiophene]–CH$_2$OH (with pendant thiophene) | 0.002 | 3.6 |

The antitumor cytotoxicity of the thiophene compounds tested in the first two in vitro assays was measured by a microculture assay using either 3-(4,5-dimethylthiazol-2-yl)-2,5-diphenyltetrazolium bromide (MTT) or sulforhodamine B (SRB). [M. R. Boyd in "Principles and Practices of Oncology," V. T. DeVita, Jr., S. Hellman and S. A. Rosenberg (Eds.), Vol. 3, PPO Updates, Number 10, 1989.] This assay has an advantage over in vivo assay in that results are obtained within a week as opposed to several months. The assay was carried out in 96-well microtiter plates. The MTT assay is based on the production of a dark blue formazan product by dehydrogenase in the mitochondria of live tumor cells after exposure to drug for 6 days [M. C. Alley, D. A. Scudiero, A. Monks, M. L. Hursey, M. J. Czerwinski, D. L. Fine, B. J. Abbott, J. G. Mayo, R. H. Shoemaker and M. R. Boyd, Cancer Res., 48, 589, 1988.] Thus, only live cells are stained and can be measured at 570 nm. The SRB assay is based on the binding of the anionic group to the basic amino acid residues of cellular proteins after exposure of tumor cells to drug for 2 days [P. Skehan, R. Storeng, D. Scudiero, A. Monks, J. McMahon, D. Vistica, J. T. Warren, H. Bohesch, S. Kenney and M. R. Boyd, J. Nat. Cancer Inst., 82, 1107, 1990.] Thus, the total protein (viability) can be measured at 564 nm. Antitumor cytotoxicity is reported as GI$_{50}$, effect drug dose at which cell growth is retarded to 50% of control culture of tumor cells. The active compounds are defined as those compounds having GI$_{50}$ values that are less than $10^{-1}$M or 10 μg/ml.

Antitumoral activity of the present polythiophene compounds has been confirmed by in vivo animal test data. The in vivo data was derived from experiments in which human tumors are transplanted into immune deficient mice and allowed to grow for two days prior to treatment with a polythiophene composition of this invention. See Example 48 and accompanying Tables 9 and 10. Data obtained from studies using heterotransplanted tumors in immune deficient mice are recognized as well-correlated with the effectiveness of these agents in clinical studies (Giovanella, B. C. et al. Cancer 52(7): 1146 (1983).

The present invention further provides pharmaceutical formulations comprising an effective amount of a polythiophene compound for treating a patient having a tumor. As used herein, an effective amount of the polythiophene compound is defined as the amount of the compound which, upon administration to a patient, inhibits growth of tumor cells, kills malignant cells, reduces the volume or size of the tumors or eliminates the tumor entirely in the treated patient.

The effective amount to be administered to a patient is typically based on body surface area, patient weight, and patient condition. The interrelationship of dosages for animals and humans (based on milligrams per meter squared of body surface) is described by Freireich, E. J., et al., Cancer Chemother. Rep., 50 (4): 219 (1966). Body surface area may be approximately determined from patient height and weight (see e.g., Scientific Tables, Geigy Pharmaceuticals, Ardley, New York, pages 537–538 (1970)). An effective amount of the polythiophene compounds in the present invention can range from about 5 mg/kg, to about 500 mg/kg, more preferably from about 5 mg/kg to about 250 mg/kg, and most preferably about 5 to about 150 mg/kg.

Effective doses will also vary, as recognized by those skilled in the art, dependant on route of administration, excipient usage and the possibility of co-usage with other therapeutic treatments including other anti-tumor agents, and radiation therapy.

The pharmaceutical formulation may be administered via the parenteral route, including subcutaneously, intraperitoneally, intramuscularly and intravenously. Examples of parenteral dosage forms include aqueous solutions of the active agent, in a isotonic saline, 5% glucose or other well-known pharmaceutically acceptable liquid carrier. In one preferred aspect of the present embodiment, the polythiophene compound is dissolved in a saline solution containing 5% of dimethyl sulfoxide and 10% Cremphor EL (Sigma Chemical Company). Additional solubilizing agents such as cyclodextrins, which form specific, more soluble complexes with the present polythiophene compounds, or other solubilizing agents well-known to those familiar with the art, can be utilized as pharmaceutical excipients for delivery of the polythiophene compounds.

The present compound can also be formulated into dosage forms for other routes of administration utilizing well-known methods. The pharmaceutical compositions can be formulated, for example, in dosage forms for oral administration in a capsule, a gel seal or a tablet. Capsules may comprise any well-known pharmaceutically acceptable material such as gelatin or cellulose derivatives. Tablets may be formulated in accordance with conventional procedure by compressing mixtures of the active polythiopene and solid carriers, and lubricants well-known to those familiar with the art. Examples of solid carriers include starch, sugar, bentonite. The compounds of the present invention can also be administered in a form of a hard shell tablet or capsule containing, for example, lactose or mannitol as a binder and a conventional fillers and tableting agents.

The following examples are provided to illustrate various embodiments of Applicants' invention, and are not intended to in any way limit the scope of the invention as set forth in this specification and appended claims.

EXAMPLE 1

Synthesis of 5-formyl-5'-heptyl-2,2'-bithiophene (NSC code #647074)

Dimethyl formamide (DMF) (8 ml) was stirred at 0° C. for 10 minutes. $POCl_3$ (1 ml) was added and then stirred for 1 hours. 5-Heptyl-2,2'-bithiophene (0.5 g) dissolved in dimethyl formamide (5 ml) was added and stirred at room temperature for half an hour at room temperature, then the temperature was raised to 60° C. and was further stirred for 4 hours. The reaction solution was then extracted with dichloromethane, neutralized with sodium acetate, washed with water to neutrality, dried, concentrated and separated by silica gel chromatography eluted with ethyl acetate/n-hexane (1/15). Light yellowish oily product (0.86 g, 86%) was obtained.

Spectral Data:

$^1$H NMR ($CDCl_3$), δ value 9.81 (s, 1H, —CHO), 6.71–7.62 (m, 4H, protons of thiophene) 2.79 (t, 2H, —C$H_2$), 0.86 (t, 3H, C$H_3$) IR (neat): $cm^{-1}$ 2910 (CH), 1665 (C=O) Mass spectrum, m/e (relative intensity) 264 ($M^+$, 44), 206 (100)

Preparation of 5-heptyl-2,2'-bithiophene

To a solution of 5-(heptan-1-one)-2,2'-bithiophene (2.0 g, 7.19 mmole) in dioxane (20 ml), a mixture of hydrochloric acid, dioxane and glacial acetic acid (15:20:15) was added. Excess of freshly prepared zinc amalgam was then added and stirred at room temperature for 2 hours. The solution mixture was then extracted with ether, neutralized with 10% sodium hydroxide aqueous solution, washed with water to neutrality, dried, concentrated and separated by silica gel chromatography eluted with n-hexane/ethyl acetate (1:20). Oily product 0.91 g (48%) was obtained.

Spectral Data:

$^1$H NMR ($CDCl_3$), δ value 6.65–7.24 (m, 5H, protons of thiophene), 1.67–1.23 (m, 2H, C$H_2$), 0.87 (t, 3H, C$H_3$) IR (neat): $cm^{-1}$ 2910 (CH) Mass spectrum, (m/e) (relative intensity) 264 ($M^+$, 24), 179 (100)

Preparation of 5-(heptan-1-one)-2,2'-bithiophene

To a solution of 2,2'-bithiophene (0.57 g, 3.43 mmole) (Aldrich Chem. Co., Milwaukee, Wis.) in benzene (10 ml) was added proper amount of phosphorous pentaoxide and was stirred at room temperature until the solution was homogeneous. Heptanoic acid (0.7 g, 5.35 mmole) was dissolved in benzene (10 ml) and added slowly to the reaction mixture. The solution was heated to 70° C. for 2 hours. The solution was extracted with ethyl acetate, washed with sodium bicarbonate aqueous solution several times, then washed with water until neutrality. The extract was dried and concentrated. The residue was separated by silica gel chromatography, eluted first with hexane to recover starting material and then with n-hexane/ethyl acetate (10:1). Light yellowish crystalline product 0.28 g (30%) was obtained, melting point 85° C.

Spectral Data:

$^1$H NMR ($CDC_3$), δ value 7.55–7.01 (m, 5H, protons of thiophene), 1.75–1.20 (m, 8H, C$H_2$), 0.85 (t, 3H, C$H_3$) IR (KBr): $cm^{-1}$ 1645 (C=O) Mass spectrum: m/e (relative intensity) 278 ($M^+$, 20), 208 (40), 193 (51), 179 (100)

EXAMPLE 2

Synthesis of (5heptyl-5'-hydroxethyl)-2,2'-bithiophene (NSC code #647450)

5-Formyl-5'-heptyl-2,2'-bithiophene (0.4 g) was dissolved in tetrahydrofuran (THF) (15 ml) and stirred at 0° C. for 10 minutes. $NaBH_4$ (0.1 g) was added at room temperature and stirred for 2 hours. Then the solution was extracted with ethyl acetate (100 ml). The extract was washed with water, then dried and concentrated. The solid product was thus obtained and further recrystallized from ethyl acetate/n-hexane mixture. Light yellowish solid product (0.21 g, 52%) was obtained and the melting point of the product was 59° C.

Spectral Data:

$^1$H NMR ($CDCl_3$), δ value 6.64–6.96 (m, 4H, protons of thiophene) 4.77–4.78 (m, 2H, OC$H_2$), 2.75 (t, 2H, C$H_2$) 1.23–1.76 (m, 2H, C$H_2$), 0.87 (t, 3H, C$H_3$) IR (KBr): $cm^{-1}$ 3250 (OH), 1070 (C—OH) Mass spectrum, m/e (relative intensity) 294 ($M^+$, 59), 209 (100)

Preparation of 5-formyl-2,2'-bithiophene

To dimethyl formamide (250 ml) was added phosphoryl chloride (50.2 ml) with quick stirring. 2,2'-Bithiophene (83 g) in dimethyl formamide (200 ml) was then added and stirred at −10° C. for 30 minutes. Then the temperature was raised to 40° C. and was further stirred for 20 hours. The reaction mixture was then poured into crushed ice and stirred for 30 minutes. Sodium hydroxide aqueous solution (10%, 600 ml) was added and the solution was extracted with chloroform. The organic layer was washed with water, dried over anhydrous magnesium sulfate, concentrated and separated by silica gel chromatography. Product 90 g was obtained, melting point 56°–57° C.

Spectral Data:

$^1$H NMR ($CDCl_3$), δ value 9.70 (s, 1H), 7.60–7.47 (m, 1H), 7.30–7.10 (m, 3H), 7.06–6.90 (m, 1H)

EXAMPLE 3

Synthesis of 5-(1-hydroxypropyl)-2,2'-bithiophene

5-Formyl-2,2'-bithiophene (3 g) was dissolved in THF (50 ml) and ethyl-magnesium bromide Grignard reagent (9.3 ml) was added dropwisely under nitrogen gas atmosphere in ice bath and stirred for 1 hour. The mixture was stirred for 1 hr. and then continuously stirred at room temperature. The reaction was monitored by thin layer chromatography. After the reaction was completed, water (30 ml) and ethyl acetate (200 ml) were added to the mixture and extracted and purified by column chromatography, eluted with ethyl acetate/n-hexane (1/9). Light yellowish product was thus obtained.

Spectral Data:

$^1$H NMR ($CDCl_3$), δ value 7.16–6.63 (m, 5H, protons of thiophene), 4.78–4.73 (t, 1H, —C$H$(OH)C$H_2$C$H_3$) 1.92–1.79 (m, 2H, —C$H_2$C$H_3$), 0.98–0.90 (t, 3H, —C$H_3$) IR (NaCl): $cm^{-1}$ 3400 (OH), 2950 (CH)

EXAMPLE 4

Synthesis of 5-(3,4-dihydroxy-1-butenyl)-2,2'-bithiophene 5-(3-Oxo-but-1-en-4-al)-bithiophene (0.5 g) and $NaBH_4$ (0.2 g) were dissolved in tetrahydrofuran (10 ml) and stirred at room temperature for 2 hours. The reaction solution was added with ethyl acetate (200 ml) and distilled water. The extract was washed with water and dried over anhydrous magnesium sulfate. After concentration, the product was separated by column chromatography, eluted with ethyl acetate/n-hexane (3/7). Light yellowish crystals were thus obtained and melting point thereof was 96°–98° C.

Spectral Data:

$^1$H NMR (400 MHz, $CDCl_3$), δ value 3.60–3.74 (dd, 2H, —$CH_2OH$), 4.40 (m, 1H, —CH(OH)), 5.98–6.06 (dd, 1H, C=CH—), 7.20–7.26 (d, 1H, —CH=C) 6.86–7.17 (m, 5H, protons of thiophene) IR (KBr): $cm^{-1}$ 3326, 3076, 1462, 1423, 1122, 960, 790, 688 Mass spectrum (12 ev), m/e (relative intensity) 252 ($M^+$, 91), 233(30), 221(100), 204 (24), 176(15)

Preparation of 5-(3-oxo-but-1-en-4-al)-2,2'-bithiophene 5-(4,4-Dimethoxy-3-oxo-1-butenyl)-2,2'-bithiophene was dissolved in methanol (40 ml). Hydrochloric acid (3N, 20 ml) was added and refluxed for 4 hours. The reaction mixture was extracted with ethyl acetate (400 ml). The extract was washed with water and sodium bicarbonate aqueous solution, dried, concentrated and separated by silica gel chromatography. Dark orange oily product was obtained.

Preparation of 5-(4,4-dimethoxy-3-hydroxy-1-butenyl)-2,2'-bithiophene

To a solution of 5-(4,4-dimethoxy-3-oxo-1-butenyl)-2,2'-bithiophene (50 mg) in tetrahydrofuran (2.5 ml) was added sodium borohydride (10 mg). The reaction mixture was stirred at room temperature for 1 hour. Ethyl acetate and water was added for partition. The organic layer was dried over anhydrous magnesium sulfate, concentrated and separated by silica gel chromatography. Light greenish oily product was obtained.

Spectral Data:

$^{13}$C NMR ($CDCl_3$), δ value 140.91, 137.49, 136.25, 127.87, 127.00, 126.42, 125.04, 124.46, 123.88, 123.71, 71.83, 55.73, 55.11 IR (neat): $cm^{-1}$ 3400 (O—H), 2950 (C—H), 1070 (C—O)

Preparation of 5-(4,4-dimethoxy-3-oxo-1-butenyl)-2,2'-bithiophene

To a solution of 5-formyl-2,2'-bithiophene (4.0 g) in ethanol (120 ml) was added dimethoxymethyl methyl ketone (3 ml). Potassium hydroxide aqueous solution (50%) was added dropwisely into the solution mixture at 16° C. Color changed from yellowish brown into dark green, then dark brown. Yellow solid was formed during the reaction. Water was added. Solid residue was filtered and washed with water, redissolved in acetone and separated by silica gel chromatography eluted with ethyl acetate/n-hexane.(1:9). Yellowish crystals 1.88 g were obtained, melting point 74° C.

Spectral Data:

$^1$H NMR ($CDCl_3$), δ value 7.82 (d, 1H, —CH=CH—), 7.27–7.03 (m, 5H, protons of thiophene), 6.77 (d, 1H, —CH=CH—), 3.43 (s, 6H, $(OCH_3)_2$) Mass spectrum, m/e 294 ($M^+$), 219 ($M^+$—$CH(OCH_3)_2$)

EXAMPLE 5

Synthesis of 5-hydroxymethyl-5''-methyl-α-terthiophene (NSC code #647072)

5-Formyl-5''-methyl-α-terthiophene (0.2 g) was dissolved in ethanol (50 ml). $NaBH_4$ (0.1 g) was added at room temperature and stirred for 30 minutes. The solution was monitored by thin layer chromatography. After the reaction was completed, 150 ml of ethyl acetate and 50 ml of water were added therein. The ethyl acetate solution was washed with water, dried and then purified by silica gel column chromatography. Light yellowish crystals were thus obtained and melting point thereof was 126°–128° C. The yield was almost quantitative.

Spectral Data:

$^1$H NMR ($CDCl_3$), δ value 7.09–6.72 (m, 6H, protons of thiophene) 4.87–4.85 (d, 2H, —$CH_2OH$), 2.54 (s, 3H, —$CH_3$) IR (KBr): $cm^{-1}$ 3300 (—OH), 2900(C—H), 1450 (conjugative C=C) Mass spectrum, m/e (relative intensity) 292 ($M^+$, 100), 275 (79), 258 (11)

Preparation of 5-formyl-5''-methyl-α-terthiophene

Phosphoryl chloride (1.0 ml) was added slowly to dimethyl formamide (30 ml) at 0° C. under nitrogen atmosphere. The mixture was further stirred for 1 hour at 0° C. 5-Methyl-α-terthiophene (0.5 g) in dimethyl formamide (5 ml) was added dropwisely into the reaction mixture and stirred at room temperature for 30 minutes. Temperature was raised to 60° C. and was further stirred for 2 hours. The reaction was monitored by thin layer chromatography until no starting material was left. The reaction mixture was then poured into potassium carbonate aqueous solution with crushed ice and extracted with ethyl acetate (200 ml). The extract was washed with water, dried, concentrated and separated by silica gel chromatography, eluted with ethyl acetate/n-hexane (1:4). The product was recrystallized from ethanol to give orange crystals (90% yield), melting point 158°–159° C.

Spectral Data:

$^1$H NMR ($CDCl_3$), δ value 9.82 (S, 1H, CHO), 7.64–6.66 (m, 6H, protons of thiophene), 2.47 (s, 3H, $CH_3$) IR (KBr): cm–1 1670 (conjugated C=O), 1450 (conjugated C=C) Mass spectrum: m/e (relative intensity) 290 ($M^+$, 100), 257 (9), 217 (7)

Preparation of 5-methyl-α-terthiophene

5-Formyl-α-terthiophene (0.5 g) was dissolved in a solution mixture of hydrochloric acid, dioxane and glacial acetic acid (1:2:1) (50 ml). Zinc amalgam (5 g) was added and stirred at room temperature for 3 hours. The reaction was monitored with thin layer chromatography until no starting material was detected, and then extracted with ethyl acetate (200 ml). The extract was washed with potassium carbonate aqueous solution, dried, concentrated and separated by silica gel chromatography eluted with n-hexane. The product was recrystallized from n-hexane to give light yellowish crystals, melting point 93°–94° C., yield 90%.

Spectral Data:

$^1$H NMR ($CDCl_3$), δ value 7.19 (m, 7H, protons of thiophene), 2.46 (s, 3H, $CH_3$) IR (KBr): $cm^{-1}$ 2900 (O—H), 1430 (conjugated C=C) Mass spectrum: m/e (relative intensity) 262 ($M^+$, 100), 239 (17), 131 (12)

Preparation of 5-formyl-α-terthiophene and 5,5''-diformyl-α-terthiophene (1) Phosphoryl chloride (1.0 ml) was added to dimethyl formamide (15 ml) and stirred for few minutes under nitrogen atmosphere. α-Terthiophene (2.48 g) (Aldrich Chem. Co., Milwaukee, Wis.) in dimethyl formamide was added slowly and then heated to 70° C. The temperature was then raised to 110° C. and further stirred for 2.5 hours. Cooled to room temperature and extracted with chloroform (100 ml). The extract was dried, concentrated and separated by silica gel chromatography eluted with chloroform/n-hexane (1:4) to give 5-formyl-α-terthiophene (1.94 g, 74.2%), melting point 141°–142° C. Further elution with chloroform/n-hexane/ethyl acetate (38:1:1) gave 5,5"-diformyl-α-terthiophene (0.13 g, 4.3%), melting point 219°–220° C. α-Terthiophene (0.13 g) was recovered.

Spectral Data:

5-formyl-α-terthiophene $^1$H NMR (CDCl$_3$), δ value 9.86 (s, 1H, CHO), 7.67(d, 1H, J=4 Hz), 7.25 (d, 2H, J=4 Hz), 7.21 (d, 2H, J=4 Hz), 7.10 (d, 1H, J=4 Hz), 7.02 (t, 1H, J=4 Hz) UV$_{max}$:

$\lambda_{max}$: 400 nm IR (KBr): cm-1 1649 (C=O), 2930(C—H) Mass spectrum: m/e 276 (M$^+$)

5,5"-diformyl-α-terthiophene $^1$H NMR (CDCl$_3$), δ value 9.86 (s, 2H, CHO), 7.67 (d, 2H, J=4 Hz), 7.30 (s, 2H), 7.27 (d, 2H, J=4 Hz) UV$_{max}$: $\lambda_{max}$: 400 nm IR (KBr): cm-1 149 (C=O) Mass spectrum: m/e 304 (M$^+$)

(2) To a solution of 5-iodo-2-formylthiophene (1.0 g) in acetonitrile (200 ml) was added 2,2'-bithiophene (0.7 g) under nitrogen and irradiated with 100W mercury lamp for 12 hours. The reaction was monitored with thin layer chromatography until no further product was produced. The solvent was removed and extracted with dichloromethane. The extract was dried, concentrated and separated by silica gel chromatography eluted first with ethyl acetate/n-hexane (1:9) to recover starting material, and then with ethyl acetate/n-hexane (3:7) to obtained 5-formyl-α-terthiophene.

EXAMPLE 6

Synthesis of 5-(propan-1-ol)-α-terthiophene (NSC code #649663)

(1) 5-(Propan-1-one)-α-terthiophene (0.6 g) was dissolved in ethanol (150 ml) and heated to dissolve completely. NaBH$_4$ (0.1 g) was added at room temperature and stirred for 3 hours. The solution was monitored by thin layer chromatography. After the reaction was completed, 50 ml of water was added and the ethanol was removed under reduced pressure. Yellowish green solid was thus obtained and melted at 89°–90° C. The yield was almost quantitative.

Spectral Data:

$^1$H NMR (CDCl$_3$), δ value 7.20–6.84 (m, 4H, protons of thiophene) 4.80–4.77 (t, 1H, —CH(OH)—CH$_2$CH$_3$), 1.93–0.94 (t, 3H, —CH$_2$CH$_3$) IR (KBr): cm$^{-1}$ 3400(—OH), 2900(—CH), 1450 (conjugative C=C) Mass spectrum, m/e (relative intensity) 304 (M$^+$, 58), 277 (100)

(2) 5-Formyl-α-terthiophene (3.5 g) was dissolved in anhydrous THF (200 ml) under nitrogen stream. Ethyl Grignard reagent (7.9 ml) was dropped in slowly in ice bath and stirred at 0° C. for 1 hour. The reaction mixture was then heated to 70° C. in oil bath for 4 hours. The solution was monitored by thin layer chromatography. After the reaction was completed, 50 ml of water and 300 ml of ethyl acetate were added to extract the crude product, which was then purified by column chromatography, eluted with ethyl acetate/n-hexane (1/9). Yellow solid was then obtained and recrystallized to give granulate crystals. The melting point of the product was 89°–90° C. and the yield was about 70%.

Preparation of 5-propan-1-one)-α-terthiophene

To a solution of α-terthiophene (5.0 g) in benzene (250 ml) was added phosphorous pentaoxide (3.1 g). Propanoic acid (1.6 g) was then added slowly at room temperature. The reaction mixture was heated to reflux and the reaction was monitored with thin layer chromatography. A little more phosphorous pentaoxide was added to complete the reaction. Potassium carbonate aqueous solution was added and extracted with ethyl acetate. The extract was dried, concentrated and separated by silica gel chromatography, eluted with ethyl acetate/n-hexane (1:19) to give yellow solid product, which was recrystallized from ethyl acetate/n-hexane (1:19) to give yellowish crystals (20% yield), melting point 136°–137° C.

Spectral Data:

$^1$H NMR (CDCl$_3$), δ value 7.58–7.00 (m, 7H, protons of thiophene), 2.89 (q, 2H, CH$_2$), 1.22 (t, 3H, CH$_3$) IR (KBr): cm$^{-1}$ 2900 (C—H), 1650 (conjugated C=O), 1440 (conjugated C=C) Mass spectrum: m/e (relative intensity) 304 (M$^+$, 73), 275 (100), 247 (21), 203 (59)

EXAMPLE 7

Synthesis of 5-formyl-5"-(prop-1-enyl)-α-terthiophene

POCl$_3$ (2 ml) was added into dimethyl formamide (30 ml) slowly under nitrogen gas atmosphere in ice bath and stirred for 1 hour. Dimethyl formamide (20 ml) solution of 5-(prop-1-enyl)-terthiophene (0.8 g) was dropped in slowly. The mixture was stirred for half an hour at room temperature, then the temperature was raised to 60° C. and was further stirred for 2 hours. The solution was monitored by thin layer chromatography. After the reaction was completed, the reaction solution was poured into sodium carbonate ice water solution. Then the solution was extracted with 300 ml of ethyl acetate. After drying and evaporation of the solvent residual solid was purified by column chromatography, eluted with ethyl acetate/n-hexane (1/9). Orange solid product was obtained and the melting point of the product was 146°–148° C. The yield was about 70%.

Spectral Data:

$^1$H NMR (CDCl$_3$), δ value 9.50 (s, 1H, —CHO), 7.65–6.74 (m, 6H, protons of thiophene) 6.47–6.43 (dd, 1H, —CH=CHCH$_3$), 6.11–6.02 (m, 1H, —CH=CH$_3$) 1.86–1.84 (d, 3H, CH$_3$) IR (KBr): cm$^{-1}$ 2900(CH), 1660 (conjugative C=O), 1440 (conjugative C=C) Mass spectrum, m/e (relative intensity) 316 (M$^+$, 100), 149 (58)

Preparation of 5-(prop-1-enyl)-α-terthiophene 5-(Propan-1-ol)-α-terthiophene (0.8 g) was dissolved in a mixture of benzene/methanol (1:1) (100 ml). Hydrochloric acid (2N, 5 ml) was added at room temperature. Heated to 50° C. for 1 hour and monitored with thin layer chromatography until no starting material was left. Ethyl acetate (250 ml) and water was added for partition. The organic layer was dried, concentrated and separated by silica gel chromatography eluted with n-hexane to give desired product.

Spectral Data:

$^1$H NMR (CDCl$_3$), δ value 7.19–6.72 (m, 7H, protons of thiophene), 6.45 (d, 1H, CH=CHCH$_3$), 6.08–5.99 (m, 1H, CH=CHCH$_3$), 1.85 (d, 3H, CH=CHCH$_3$) IR (KBr): cm$^{-1}$2850 (C—H), 1430 (conjugated C=C)

EXAMPLE 8

Synthesis of 5-hydroxymethyl-5"-(prop-1-enyl)-α-terthiophene 5-(Prop-1-enyl)-5"-formyl-α-terthiophene (0.4 g) was dissolved in ethanol (50 ml). NaBH$_4$ (0.1 g) was added at room temperature and stirred for 2 hours. The solution was monitored by thin layer chromatography. After the reaction was completed, water (50 ml) was added and the ethanol was removed under reduced pressure. Then the solid precipitate was extracted with 200 ml of ethyl acetate. The residual solid was purified by column chromatography, eluted with ethyl acetate/n-hexane (3/7). Yellowish solid product was obtained and melting point thereof was 132°–134° C. The yield was nearly 100%.

Spectral Data:

$^1$H NMR (CDCl$_3$), δ value 7.20–6.60 (m, 6H, protons of thiophene) 6.46–6.42 (dd, 1H, —CH=CH—CH$_3$), 6.06–6.01 (m, 1H, —CH=CH—CH$_3$) 4.79–4.78 (d, 2H, —CH$_2$OH), 1.85–1.84 (d, 3H, —CH$_3$) IR (KBr): cm$^{-1}$ 3400 (OH), 2900 (CH), 1440 (conjugative C=C) Mass spectrum, m/e (relative intensity) 318 (M$^+$, 100), 301 (26), 261 (40)

EXAMPLE 9

Synthesis of 5-ethyl-α-terthienylmethyl ether (1) 5-Formyl-α-terthiophene (0.3 g) was dissolved in ethanol (20 ml) by stirring at room temperature. To the solution, 0.04 g of NaBH$_4$ was slowly added. After the solution became clear in about 20 minutes, diluted hydrochloric acid was slowly added until bubbling stopped. The stirring was continued for about 12 hours, followed by chloroform extraction and silica gel column chromatography eluted with ethyl acetate/n-hexane (1/19). The product was recrystallized from chloroform/ethyl acetate mixture to give light yellowish platelet crystals (melting point 76°–77° C.). The yield was about 41%.

(2) The yield could be increased to 85% or higher by substituting absolute ethanol for alcohol and concentrated hydrochloric acid for diluted hydrochloric acid.

(3) 5-Formylterthiophene (2.9 g) was dissolved in absolute ethanol (75 ml). NaBH$_4$ (0.5 g) was added and stirred for 10 minutes. The solution became clear-yellow. Phosphorus oxychloride (2.5 ml) was added to an absolute ethanol and was dropped into aforementioned mixture and stirred under the nitrogen atmosphere overnight. Then the solution was extracted with ethyl acetate. The extract was washed with water and dried over anhydrous magnesium sulfate. The solvent was removed under reduced pressure. The residual solid was purified by column chromatography. Light yellowish crystals were obtained and the melting point thereof was 76°–77° C. The yield was 85%.

Spectral Data:

$^1$H NMR (CDCl$_3$), δ value 7.20–6.87 (m, 7H, protons of thiophene), 4.62 (s, 2H, —CH$_2$OC$_2$H$_5$) 3.55 (q, 2H, —CH$_2$OCH$_2$CH$_3$), 1.25 (t, 3H, —OCH$_2$CH$_3$) IR (KBr): cm$^{-1}$ 3050 (aromatic CH), 2971, 2852 (saturated CH), 1091 (C—O) Mass spectrum, m/e (relative intensity) 306 (M$^+$, 100), 261 (M$^+$—OC$_2$H$_5$, 33)

EXAMPLE 10

Synthesis of ethyl 5-(2,2'-bithienyl)-α-cyanoacrylate

5-Formyl-2,2'-bithiophene (3.9 g), cyano-ethyl-acetate (2.4 ml), pyridine (15 ml) and piperidine (2.4 ml) were mixed together at 80°–85° C. for 2 hours. After cooling, the mixture was acidified by diluted HCl and then filtered. Orange solid was thus obtained and recrystallized from ethanol to give crystalline product (5.02 g). The melting point of the product was 131° C. The yield was 86%.

Spectral Data:

IR (KBr): cm$^{-1}$ 2218, 1687 (—CN) 1699, 1687 (C=O) 1630 (thiophene) Mass spectrum, m/e (relative intensity) 289(M$^+$)

EXAMPLE 11

Synthesis of methyl 4-(2,2'-bithiophene-5-yl)-2-oxo-but-3-enoate 4-(Bithiophen-5-yl)-2-oxo-but-3-enoic acid (0.62 g) was dissolved in a mixture of methanol (25 ml) and benzene (15 ml). A trace amount of p-toulenesulfonic acid was added and heated for 6 hours. The solution was monitored by thin layer chromatography. After the reaction was completed, the solution was extracted with ethyl acetate and the extract was washed with water and NaHCO$_3$ solution. The residual solid after evaporation was purified by column chromatography, eluted with ethyl acetate/n-hexane (1/9). Light yellowish crystals (0.63 g) were obtained and the melting point of the product was 78° C. The yield was 97%.

Spectral Data:

$^1$H NMR (CDCl$_3$), δ value 7.90–7.94 (d, 1H, —CH=CH—) 6.91–7.31 (m, 6H, —CH=CH—, protons of thiophene) 3.89 (s, 3H, —COOCH$_3$) IR (KBr): cm$^{-1}$ 1730, 1690 (C=O) 1650, 1600, 1580 (conjugative unsaturated bonding) Mass spectrum (75 ev), m/e (relative intensity) 278(M$^+$, 16), 265 (100), 219 (93)

EXAMPLE 12

Synthesis of 5-α-terthienylmethylidene malonic acid

5-Formyl-α-terthiophene (1.30 g), malonic acid (1.04 g), pyridine (20 ml) and of pyrrole (0.1 ml) were mixed together at 50°–60° C. for 2 hours. Water (100 ml) was added after reaction was completed. The mixture was acidified by diluted HCl and then filtered. Red solid thus obtained was recrystallized from ethanol to give 1.43 g of the product and the melting point thereof was 202°–203° C. The yield was 84%.

EXAMPLE 13

Synthesis of 5-(3-hydroxy-1-propynyl)-2,2'-bithiophene

Hydroxy-1-propyne (48 mg) was dissolved in benzene (1 ml). 5-Iodo-2,2'-bithiophene (0.1 g) was added immediately and stirred. A mixture of CuI (0.05 g), benzyltriethylammonium chloride (0.05 g), catalyst Pd(PPh$_3$)$_4$ (0.1 g) and 3 ml of NaOH solution (2.5N) were mixed together at room temperature and stirred for 2 hours. NH$_4$Cl solution (4 ml) was then added. The reaction solution was extracted with ethyl acetate. The extract was washed with 10 ml of HCl (10%) for 3 times, 50 ml of water twice and dried over anhydrous magnesium sulfate. The residual solid was purified by silica gel column chromatography, eluted with ethyl acetate/n-hexane (3/1) to yield 56 mg of the product (74%).

Spectral Data:

$^1$H NMR 400 MHz (CDCl$_3$), δ value 2.3 (b, 1H, —OH), 4.5 (s, 2H, —CH$_2$) 6.9–7.3 (m, 5H, protons of thiophene) $^{13}$C-NMR (CDCl$_3$), δ value 51.50, 78.89, 92.19, 121.11, 123.48, 128.06, 133.4, 136.70, 139.25 IR (neat): cm$^{-1}$ 3350 (OH), 2250 (C≡C)

Preparation of 5-iodo-2,2'-bithiophene and 5,5'-diiodo-2,2'-bithiophene

To a solution of 2,2'-bithiophene (33.2 g) in ethanol (50 ml) was added iodine (20.3 g) in ethanol (200 ml). Then iodine (V) oxide (6.7 g) in ethanol (30 ml) was added dropwisely. The reaction mixture was further stirred at room temperature for 5 hours. Ethanol was removed and the residue was dissolved in dichloromethane. The solution was washed with sodium bicarbonate aqueous solution (10%, 150 ml×2) then water (200 ml×2). Dried over anhydrous magnesium sulfate and concentrated to give crude products. Distilled under vacuum (105°–110° C./0.1 mm Hg) to give 5-iodo-2,2'-bithiophene (36.8 g, 63%). The residue was then separated by silica gel chromatography eluted with n-hexane to give 5,5'-diiodo-2,2'-bithiophene (5.36 g, 6.4%), melting point 170° C.

Spectral Data:

5-iodo-2,2'-bithiophene $^1$H NMR (CDCl$_3$), δ value 7.20 (m, protons of thiophene) Mass spectrum, m/e (relative intensity) 292 (M$^+$, 100), 165 (M$^+$—I, 14) 5,5'-diiodo-2,2'-bithiophene $^1$H NMR (CDCl$_3$), δ value 7.05 (d), 6.7 (d) Mass spectrum, m/e (relative intensity) 4.18 (M$^+$, 100), 291 (M$^+$—I, 9)

EXAMPLE 14

Synthesis of 5-(2,2'-bithiophene-5-yl)-prop-2-yn-1-ol-acetate 5-(3-Hydroxy-1-propyne)-2,2'-bithiophene (0.8 g) was dissolved in acetic anhydride (0.5 ml) and pyridine (1.5 ml) at room temperature and stirred for 2 hours. The reaction solution was extracted with ethyl acetate. The extract was washed with 10 ml of HCl (10%) for 3 times, 10 ml of NaOH solution for 3 times, 50 ml of water twice and dried over anhydrous magnesium sulfate. The residual solid after evaporation was purified by silica gel column chromatography eluted with ethyl acetate/n-hexane (1/10). Light brownish-yellow oily product (0.71 g, 73%) was obtained.
Spectral Data:

$^1$H NMR (CDCl$_3$), δ value 2.11 (s, 3H, —CH$_3$), 4.90 (s, 2H, —CH$_2$) 6.97–7.22 (m, 5H, protons of thiophene) IR (neat): cm$^{-1}$ 2250 (C≡C), 1745 (C=O), 1225 Mass spectrum, m/e (relative intensity) 262 (M$^+$, 100), 202 (65)

EXAMPLE 15

Synthesis of ethyl-5-α-terthienylpropiolate

Ethyl propiolate (78 mg) was dissolved in benzene (3 ml). 5-Iodo-α-terthiophene (0.2 g) was added immediately and stirred. A mixture of CuI (0.05 g), benzyltriethylammonium chloride (0.05 g), catalyst Pd(PPh$_3$)$_4$ (0.1 g) and 5 ml of NaOH solution (2.5N) were mixed together. The temperature of the mixture was then raised to 40° C. and stirred for 5 more hours. Then 5 ml of NH$_4$Cl solution was added. The reaction solution was extracted with ethyl acetate. The extract was washed with 10 ml of HCl (10%) 3 times, 50 ml of water twice and dried over anhydrous magnesium sulfate. The residual solid after evaporation was purified by silica gel column chromatography, eluted with ethyl acetate/n-hexane (1/15). Light brown product (78 mg, 42%) was then obtained and the melting point thereof was 93° C.
Spectral Data:

$^1$H NMR (CDCl$_3$), δ value 1.35 (t, 3H, —CH$_3$), 4.31 (q, 2H, —CH$_2$) 6.90–7.41 (m, 5H, protons of thiophene) IR (KBr): cm$^{-1}$ 2200 (C≡C), 1705 (C=O) Mass spectrum, m/e (relative intensity) 344 (M$^+$, 17), 248(100)

Preparation of 5-iodo-α-terthiophene

α-Terthiophene (2.33 g) was dissolved in ethanol (70 ml). Iodine (1.10 g) in ethanol (25 ml) was added and then iodic acid (0.47 g) in water (1.0 ml) was added dropwisely and the temperature was kept below 31° C. The reaction mixture was further stirred for 4 hours. Precipitate from the reaction was filtered and recrystallized to give product (97.3% yield), melting point 146°–148° C.

EXAMPLE 16

Synthesis of 5-α-terthienylacrylic acid (NSC code #637391)

5-Formyl-α-terthiophene (276 mg), malonic acid (0.212 g), pyridine (10 ml), and piperidine (1 ml) were mixed together at water bath for 2 hours and cooled for 30 minutes at room temperature. The reaction solution was then poured into water. The mixture was acidified by diluted HCl. After standing at room temperature for 3 hours, the reddish-brown solid was filtered, washed with water and recrystallized from 95% of ethanol to give copper red needle-like crystals and the melting point thereof was 237°–238° C. The yield was 78.6%.
Spectral Data:

UV: λmax: 395 nm IR (KBr): cm$^{-1}$ 3200–2300 (OH), 1672 (C=O), 1616 (CH=CH) $^1$H NMR (d$_6$-DMSO): δ value 6.13 (1H,—CH=CH—COOH, d, J=16), 7.70 (1H, —CH=CH—COOH, d, J=16) 7.1–7.6 (m, 7H, protons of thiophene) Mass spectrum, m/e (relative intensity) 318(M$^+$)

EXAMPLE 17

Synthesis of methyl 4-(α-terthiophene-α-5-yl)-2-oxo-but-3-enoate 4-(α-Terthiophene-α-5-yl)-2-oxo-but-3-enoic acid (0.2 g) was dissolved in ethanol (20 ml). A trace amount of p-toluenesulfonic acid was added and refluxed overnight. Then the solution was extracted with ethyl acetate. The extract was purified by column chromatography, eluted with ethyl acetate/n-hexane (1/9). Dark reddish crystal product was then obtained.
Spectral Data:

$^1$H NMR (CDCl$_3$), δ value 7.9–7.94 (d, 1H, —CH=CH—) 7.01–7.32 (m, 8H, —CH=CH—, protons of thiophene) 3.91 (s, 3h, —COOCH$_3$)

Mass spectrum (75 ev): m/e (relative intensity) 360 (M$^+$, 53), 301 (100), 282 (23)

Preparation of 4-(2,2'-bithien-5-yl)-2-oxo-but-3-enoic acid

To a solution of 5-formyl-2,2'-bithiophene (5.0 g) in ethanol (70 ml) was added a solution of sodium pyruvate (3.4 g) in water (5 ml). The reaction mixture was stirred at room temperature for 10 minutes. Sodium hydroxide aqueous solution (50%) was then added and further stirred for 3 hours at room temperature. Precipitate was filtered and washed with ether. The solid was dissolved in hydrochloric acid and extracted with ethyl acetate. The extract was dried and filtered through silica gel, concentrated to give dark red crystals (5.3 g, 78%), melting point 136°–142° C.
Spectral Data:

$^1$H NMR (CDCl$_3$+DMSO-d$_6$), δ value 7.86 (d, 1H, CH=CH), 7.28–6.91 (m, 6H, CH=CH and protons of thiophene) IR (KBr): cm$^{-1}$ 3500–2500 (COO—H), 1720, 1670 (C=O), 1580 (C=C) Mass spectrum: m/e (relative intensity) 264 (M$^+$, 37), 219 (100)

EXAMPLE 18

Synthesis of 5-formyl-α-tetrathiophene (NSC code #645273)

Dimethyl formamide (30 ml) was stirred and cooled in ice bath for 10 minutes. POCl$_3$ (0.2 ml) was added into the solution at 0° C. and stirred for 1 hour. Dimethyl formamide (20 ml) solution of α-tetrathiophene (0.5 g) was dropped in slowly. The mixture was stirred for 1 hour at 0° C., then the temperature was raised to room temperature, and further stirred for 8 hours at 70° C. The cold reaction solution was poured into NaOH ice water solution, and extracted with dichloromethane. The extract was washed with 50 ml of water for 3 times, dried over anhydrous magnesium sulfate and concentrated. The residual solid was further purified by silica gel column chromatography, eluted with n-hexane/tetrahydrofuran (1/1). Dark yellow solid (0.22 g, 41%) product was obtained after recrystallization from n-hexane and tetrahydrofuran. The melting point of the product was 215° C.

Spectral Data:

$^1$H NMR (CDCl$_3$), δ value 7.00–7.66 (m, 5H, protons of thiophene) 9.84 (s, 1H, —CHO) IR (KBr): cm$^{-1}$ 1665 (C=O) Mass spectrum, m/e (relative intensity) 358 (M$^+$, 100)

Preparation of α-tetrathiophene

5-Iodo-2,2'-bithiophene (10 g, 34.2 mmole) and copper powder (2.8 g, 44.0 mmole) was mixed together. Dimethyl formamide (20 ml) was added and heated to reflux for 6 hours. The reaction mixture was extracted with tetrahydrofuran and decanted to separate the unreacted copper powder. The solvent was removed and the residue was separated by silica gel chromatography eluted first with n-hexane to recover starting material and then with n-hexane/tetrahydrofuran (2:1) to give product. Light yellowish crystals were obtained after recrystallization (34.8% yield), melting point 208° C.

EXAMPLE 19

Synthesis of 5-hydroxymethyl-α-tetrathiophene (NSC code # 645274)

5-Formyl-α-tetrathiophene (180 mg) was dissolved in dimethyl formamide (10 ml) solution. NaBH$_4$ (0.1 g) was then added. The mixture was stirred for 2 hours at room temperature. Then the solution was extracted with dichloromethane and washed with 10 ml of water twice and dried over anhydrous magnesium sulfate. After evaporation the residual solid was purified by silica gel column chromatography and further recrystallized from THF and n-hexane. Light orange solid (150 mg, 82.4%) was obtained and the melting point of the product was 216° C.

Spectral Data:

IR (KBr): cm$^{-1}$ 3300 (OH) Mass spectrum, m/e (relative intensity) 360 (M$^+$, 100) 344 (21)

EXAMPLE 20

Synthesis of 5-(4-hydroxy-1-butynyl )-2,2'-bithiophene (1) Hydroxy-1-butyne (0.23 g) was dissolved in benzene (1 ml). 5-Iodo-2,2'-bithiophene (0.3 g) was added immediately and stirred. CuI (0.05 g), benzyltriethylammonium chloride (0.05 g), Pd(PPh$_3$)$_4$ (0.1 g) and NaOH solution (2.5N) (4 ml) were mixed together at room temperature and stirred for 2 hours. NH$_4$Cl solution (5 ml) was then added. The reaction solution was extracted with ethyl acetate. The extract was washed with 10 ml of HCl (10%) for 3 times, 50 ml of water twice and dried over anhydrous magnesium sulfate. The residual solid after evaporation was purified by silica gel column chromatography, eluted with ethyl acetate/n-hexane (1/3). Light yellowish product (0.21 g, 75%) was obtained and the melting point thereof was 67° C.

(2) In a brown three-necked round bottom flask equipped with condenser, thermometer and nitrogen inlet was added 5-iodo-2,2'-bithiophene (17.07 g) and pyridine (100 ml). 3-Butyne-1-ol cuperous salt was quickly added and refluxed under nitrogen atmosphere for 3.5 hours. Pyridine was then distilled and the reaction mixture was extracted with dichloromethane (100 ml×2). The extract was washed with water (150 ml×2), 10% sodium bicarbonate aqueous solution (100 ml×2) and again water (150 ml×2) to remove water soluble compounds. The organic layer was dried over anhydrous magnesium sulfate, concentrated and separated by silica gel chromatography eluted with n-hexane to recover starting material (3.56 g) and then with n-hexane/ethyl acetate (6:1) to give light yellowish crystalline product (8.49 g, 62%).

Spectral Data:

$^1$H NMR (CDCl$_3$), δ value 7.20–6.75 (m, 5H, protons of thiophene), 3.7 (t, 2H, C$\underline{H}_2$OH), 2.7 (t, 2H, C$\underline{H}_2$CH$_2$OH) IR: cm$^{-1}$ 3300 (br, O—H), 1032 (C—O) Mass spectrum: m/e (relative intensity) 234 (M$^+$17) 203 (M$^+$—CH$_2$OH, 10), 84 (100)

EXAMPLE 21

Synthesis of 5-(4-acetoxy-1-butynyl)-2,2'-bithiophene 4-(Hydroxy-1-butynyl)-2,2'-bithiophene (1.23 g) was dissolved in pyridine (6 ml). Acetic anhydride (1 ml) was added at room temperature, stirred for few minutes and further kept overnight. Water (20 ml) was added oily product was then extracted with 30 ml of ethyl acetate. The extract was washed with 10 ml of HCl (1N) for 3 times, 10 ml of water once and 10 ml of diluted KHCO$_3$ solution once. Ethyl acetate was then reproved under reduced pressure. The residual solid was purified by silica gel column chromatography, eluted with ethyl acetate/n-hexane (1/19). Light yellowish oily product (1.7 g) was obtained after removal of the solvent.

Spectral Data:

$^1$H NMR: δ value 7.3–6.8 (m, 5H, protons of thiophene), 4.16 (t, 2H, —CH$_2$—CH$_2$—O—) 2.7 (t, 2H, —CH$_2$—CH$_2$—O—), 2.0 (t, 3H, —OCOC$\underline{H}_3$) IR: cm$^{-1}$ 3035 (aromatic C—H) 2960, 2900 (adipose C—H) 1737, 1232, 1038 (ester) Mass spectrum, m/e (relative intensity) 276 (M$^+$, 46), 216 (M$^+$—AcOH, 100)

EXAMPLE 22

Synthesis of 5-(4-isovaleryloxy-1-butynyl)-2,2'-bithiophene 5-(4-Hydroxy-1-butynyl)-2,2'-bithiophene (1 g) was dissolved in pyridine (10 ml). Isovaleroyl chloride (1 ml) was added at room temperature, stirred for few minutes and kept overnight. The reaction mixture was treated as in example 21. Light yellowish oily product (1.06 g) was then obtained.

Spectral Data:

$^1$H NMR: δ value 6.95–7.1 (m, 5H, protons of thiophene), 4.2 (t, 2H, J=7 Hz, —CH$_2$—C$\underline{H}_2$—O—) 2.72 (t, 2H, J=7 Hz, —C$\underline{H}_2$—CH$_2$—O—), 2.18 (br.s. 2H, —O—CO—C$\underline{H}_2$—) 2.2–1.9 (m, 1H, —CH$_2$—C$\underline{H}$(CH$_3$)$_2$), 0.96 (1, 6H, J=6 Hz, CH(C$\underline{H}_3$)$_2$) IR: cm$^{-1}$3100, 3070 (aromatic C—H), 2960–2870 (aliphatic C—H) 1730, 1250, 1150 (ester) 1460, 1380, 1360 (—CH(CH$_3$)$_2$) 834, 795, 692 (2,2'-bithiophene) Mass spectrum, m/e (relative intensity) 318 (M$^+$, 15), 216 (M+—(CH$_3$)$_2$CHCH$_2$COOH, 100)

EXAMPLE 23

Synthesis of 5-(4-benzoxy-1-butynyl )-2,2'-bithiophene 5-(4-Hydroxy-1-butynyl)-2,2'-bithiophene (0.8 g) was dissolved in pyridine (8 ml). Benzoyl chloride (1 ml) was added at room temperature, stirred for few minutes and kept overnight. The reaction mixture was treated as in example 21. Light yellowish crystals were then obtained and the melting point thereof was 61° C.

Spectral Data:

$^1$H NMR: δ value 6.86–8.28 (m, 10H, aromatic H) 4.42 (t, 2H, —CH$_2$—C$\underline{H}_2$—O—), 2.85, (t, 2H, —C$\underline{H}_2$—CH$_2$—O—) IR: cm$^{-1}$ 3090, 3040 (aromatic C—H) 1695, 1268, 1109 (aromatic ester) Mass spectrum, m/e (relative intensity) 388 (M$^+$, 16), 216 (M$^+$—C$_6$H$_5$COOH, 100)

EXAMPLE 24

Synthesis of 5-(4-palmityloxy-1-butynyl)-2,2'-bithiophene 5-(4-Hydroxy-1-butynyl)-2,2'-bithiophene (0.6 g) was dissolved in pyridine (10 ml). Palmitoyl chloride (1 ml) was added at room temperature, stirred for few minutes and kept overnight. The reaction mixture was treated as in example 21, and 1.2 g of light yellowish crystals were then obtained and the melting point thereof was 68°–69° C.

Spectral Data:

$^1$H NMR: δ value 7.26–6.84 (m, 5H, protons of thiophene) 4.25 (t, 2H, —CH$_2$—O—), 2.67 (t, 2H, —CH$_2$—CH$_2$—O—) 2.28 (t, 2H, —OCOCH$_2$C$_{14}$H$_{29}$), 1.22 broad (m, 29H, —OCOCH$_2$C$_{14}$H$_{29}$) IR: cm$^{-1}$ 3030 (aromatic C—H), 2950, 2840 (aliphatic C—H) 1730, 1170 (ester) Mass spectrum, m/e (relative intensity) 472 (M$^+$, 25), 216 (M$^+$—C$_{15}$H$_{31}$COOH, 100)

EXAMPLE 25

Synthesis of 5-(3-hydroxy-4-pyranyloxy)-1-butynyl-2,2'-bithiophene 4-(Tetrahydropyranyloxy)-3-hydroxy-butyne (6.7 g) was dissolved in benzene (20 ml). 5-Iodo-2,2'-bithiophene (5.75 g) was added immediately and stirred. A mixture of CuI (0.15 g) and benzyltriethylammonium chloride (0.14 g, 0.63 mmole) was added. Pd(PPh$_3$)$_4$ (0.46 g, 0.398 mmole) was then added. NaOH solution (30 ml, 2.5N) was added slowly into the mixture at room temperature in water bath for 2 hours. NH$_4$Cl solution (10 ml) was added. The reaction solution was extracted with ethyl acetate. The extract was washed with 10 ml of HCl (10%) for 3 times, 50 ml of water for 3 times and dried over anhydrous magnesium sulfate. The residual solid after evaporation was purified by silica gel column chromatography, eluted with ethyl acetate/n-hexane (1/3). Reddish oily product (6.25 g, 95%) was then obtained.

Spectral Data:

$^1$H NMR (CDCl$_3$), δ value 1.4–1.9 (m, 6H, 3CH$_3$), 3.3–4.0 (m, 4H, 2CH$_2$) 4.5–4.7 (m, 1H, CH), 6.9–7.2 (m, 5H, protons of thiophene) IR (neat): cm$^{-1}$ 3400 (OH), 2950(C—H), 2250(C≡C) Mass spectrum, m/e (relative intensity) 334(80, M$^+$), 304(41), 234(49), 190(51), 86(100)

Preparation of 3-hydroxy-4-(tetrahydro-2-pyranyloxy)-butyne

Acetylene gas was bubbled into tetrahydrofuran (30 ml) for 30 minutes. Ethyl magnesium bromide (25 ml) was added. 2-(Tetrahydro-2-pyranyloxy)-acetaldehyde (5.0 g, 0.035 mole) in tetrahydrofuran (25 ml) was then added. The reaction mixture was warmed to room temperature and stirred overnight. Saturated ammonium chloride aqueous solution (30 ml) was added to quench the unreacted acetylide and extracted with ethyl acetate. The extract was dried over anhydrous magnesium sulfate, concentrated and separated by silica gel chromatography eluted with n-hexane/ethyl acetate (5:2) to give colorless oil (4.5 g, 76%).

Spectral Data:

$^1$H NMR (CDCl$_3$), δ value 4.6–4.4 (m, 2H, 2CH), 3.8–3.6 (m, 2H, CH$_2$), 3.5–3.4 (m, 2H, CH$_2$) 2.4 (s, 1H, C≡CH), 1.9–1.4 (m, 4H, 2CH$_2$) IR (neat): cm$^{-1}$ 3600–3000 (O—H), 2150 (C≡C) Mass spectrum: m/e (relative intensity) 169 (M$^+$–1), 115 (13), 97 (19), 85 (100), 56 (48)

Preparation of 2-(tetrahydro-2-pyranyloxy)-acetaldehyde 2-(Tetrahydro-2-pyranyloxy)-propene (20 g, 0.14 mole) was dissolved in dichloro-methane (250 ml). Ozone was bubbled into the solution at −78° C. for about 3 hours until the solution turned blue. Warmed to room temperature and zinc powder (20 g) was added. Acetic acid (20 ml) and water (3 ml) were added slowly with cooling in ice bath. The reaction mixture was further stirred for 2 hours at room temperature and then extracted with dichloromethane. The extract was washed with sodium bicarbonate aqueous solution (10 ml×2), dried over anhydrous magnesium sulfate, concentrated. The crude product was distilled under vacuum (62°–64° C./2 mmHg) gave colorless oil (13.72 g, 68%). 2-(Tetra-hydro-2-pyranyloxy)-propene was directly prepared from allyl alcohol and dihydropyran in the presence of a small amount of p-toluenesulfonic acid.

Spectral Data:

$^1$H NMR (CDCl$_3$), δ value 9.7 (s, 1H, CHO), 4.6 (t, 1H, O—CH—O), 1.9–1.3 (m, 6H, CH$_2$) $^{13}$C NMR (CDCl$_3$), δ value 200.78, 100.89, 74.29, 63.89, 31.39, 26.35, 20.35 IR (neat): cm$^{-1}$ 2950 (C—H), 1735 (C=O)

EXAMPLE 26

Synthesis of 5-(3-acetoxy-4-tetrahydropyranyloxy)-1-butynyl-2,2'-bithiophene 3-Acetoxy-4-tetrahydropyranyloxy-1-butyne (4.73) was dissolved in benzene (15 ml). 5-Iodo-2,2'-bithiophene (5.15 g) was added immediately and stirred. A mixture of CuI (0.13 g), benzyltriethylammonium chloride (0.12 g) and catalyst Pd(PPh$_3$)$_4$ (0.4 g) was then added. NaOH solution (20 ml, 2.5N) was added slowly into the mixture at room temperature for 2 hours. Saturated NH$_4$Cl solution (8 ml) was added. The reaction mixture was extracted with ethyl acetate. The extract was washed with 10 ml of HCl (10%) twice, 50 ml of water twice and dried over anhydrous magnesium sulfate. The residual solid after evaporation was purified by silica gel column chromatography, eluted with ethyl acetate/n-hexane (1/3). Light orange product (4.1 g, 67%) was obtained.

Spectral Data:

$^1$H NMR (CDCl$_3$), δ value 1.4–1.9 (m, 6H, 3CH$_3$), 2.1 (s, 3H, CH) 3.7–4.0 (m, 4H, 2CH$_2$), 4.7–4.8 (s, 1H, OCHO) 5.7–5.9 (m, 1H, CH), 7.0–7.3 (m, 5H, protons of thiophene) IR (neat): cm$^{-1}$ 2950 (C—H), 2225 (C≡C), 1750 (C=O) Mass spectrum, m/e (relative intensity) 376 (M$^+$, 69) 333 (21) 275(30) 234(100)

Preparation of 3-acetoxy-4-(tetrahydro-2-pyranyloxy-butyne

3-Hydroxy-4-(tetrahydro-2-pyranyloxy)-butyne (8.0 g, 0.047 mole) was mixed with acetic anhydride (10 g, 0.098 mole) and pyridine (8 g, 0.098 mole). The solution was stirred at room temperature for 1 hour and then extracted with ethyl acetate. The extract was sequentially washed with 10% hydrochloric acid (10 ml×5), saturated sodium bicarbonate aqueous solution (10 ml×5) and water (50 ml×3). The extract was dried over anhydrous magnesium sulfate, concentrated and separated by silica gel chromatography, eluted with n-hexane/ethyl acetate (5:1) to give colorless oil (9.0 g, 90%).

EXAMPLE 27

Synthesis of 5-(3-acetoxy-4-hydroxy-1-butynyl)-2,2'-bithiophene (NSC code #645277)

5-(3-Acetoxy-4-tetrahydropyranyloxy-1-butynyl)-2,2'-bithiophene (2.8 g) was dissolved in methanol (40 ml). H$_2$SO$_4$ solution (3 ml, 2N) was added slowly in ice bath and stirred at room temperature for 2 hours. The reaction solution was extracted with ethyl acetate. The extract was thus washed with 10 ml of NaHCO$_3$ three time, 50 ml of water twice and dried over anhydrous magnesium sulfate. After removal of solvent residual solid was purified by silica gel column chromatography, eluted with ethyl acetate/n-hexane (1/3). Light brown product (1.83 g, 84%) was obtained.
Spectral Data:
$^1$H NMR (CDCl$_3$), δ value 2.15 (s, 3H, —CH$_3$), 3.90 (d, 2H, —CH$_2$) 5.71 (t, 1H, CH), 7.0–7.3 (m, 5H, protons of thiophene) IR (neat): cm$^{-1}$ 3450 (OH), 2250 (C° C.), 1730 (C=O)

EXAMPLE 28

Synthesis of 5-(3,4-diacetoxy-1-butynyl)-2,2'-bithiophene 5-(3-Acetoxy-4-hydroxy)-butynyl-2,2'-bithiophene (1.83 g) was dissolved in pyridine (1.5 g) and acetic anhydride (1.27 g) at room temperature for 2 hours. The reaction solution was extracted with ethyl acetate. The extract was washed with 10 ml of HCl (10%) for 3 times, 10 ml of KHCO$_3$ solution for three times and 50 ml of water twice. The solution was then dried over anhydrous magnesium sulfate. After removal of solvent residual solid was purified by silica gel column chromatography, eluted with ethyl acetate/n-hexane (1/5). Greenish yellow oily product (1.91 g, 91%) was then obtained.
Spectral Data:
$^1$H NMR (CDCl$_3$), δ value 2.07 (s, 3H, —CH$_3$), 2.12 (s, 3H, —CH$_3$) 4.25–4.45 (m, 2H, CH$_2$), 5.80–5.87 (m, 1H, CH) IR (neat): cm$^{-1}$ 2250 (C≡C), 1755 (C=O), 1735 (C=O) Mass spectrum, m/e (relative intensity) 334 (M$^+$, 75), 274(100), 232(55)

EXAMPLE 29

Synthesis of 5,5'-dihydroxymethyl-2,2'-bithiophene (NSC code #647452)

(1) 5-Hydroxymethyl-5'-formyl-2,2'-bithiophene (0.2 g) was dissolved in ethanol (50 ml). NaBH$_4$ (0.1 g) was added at room temperature and stirred for 1 hour. The reaction was monitored by thin layer chromatography. After the reaction was completed, H$_2$O (50 ml) was added and the ethanol was removed under reduced pressure. Light yellowish solid product was obtained. The yield was almost quantitative and the melting point of the product was 158°–160° C.
Spectral Data:
$^1$H NMR (d$_6$-acetone) 7.03–6.87 (m, 4H, protons of thiophene) 4.73 (s, 4H, —CH$_2$OH) IR (KBr): cm$^{-1}$ 3500–3300 (OH), 3050 (aromatic CH) 2909, 2850 (aliphatic CH) Mass spectrum, m/e (relative intensity) 226 (M$^+$, 100), 209 (M$^+$—OH, 73)

(2) 5-Hydroxymethyl-5'-formyl-2,2'-bithiophene (0.6 g) was dissolved in tetra-hydrofuran (30 ml), NaBH$_4$ (0.16 g) was added, and the solution was stirred for 2 hours at room temperature. The solvent was removed under reduced pressure. White solid obtained was washed with water and dried under reduced pressure. The yield was quantitative. The melting point of the product was 155°–156° C.

(3) 5-Hydroxymethyl-5'-formyl-2,2,-bithiophene (0.5 g) was reduced in ethanol (75 ml) with NaBH$_4$ (0.3 g). The mixture was stirred for 3 hours at room temperature. The solution was concentrated and n-hexane was added to obtain white product. The product was washed with water, dried under reduced pressure and the yield was quantitative. The melting point of the product was 155°–156° C.

(4) 2-Hydroxymethyl-5-iodothiophene was refluxed with Cu powder in dimethyl formamide. The Ullmann condensation also produced 5,5'-dihydroxy-methyl-2,2'-bithiophene in low yield.

(5) The Ullmann condensation of 2-acetoxymethyl-5-iodothiophene gave 5,5'-diacetoxymethyl-2,2'-bithiophene. The 5,5'-dihydroxymethyl-2,2'-bithiophene was obtained by alkaline hydrolysis of diacetoxy compound and purified by column chromatography. The yield was about 20%.

EXAMPLE 30

Synthesis of 5,5'-diacetoxymethyl-2,2'-bithiophene 5,5'-Dihydroxymethyl-2,2'-bithiophene (0.23 g), pyridine (1.2 ml) and acetic anhydride (0.3 ml) were mixed, stirred and kept overnight. Then the mixture was extracted with ethylacetate. The pyridine and acetic acid were removed by washing with weak base, weak acid and water, respectively. Silica gel powder was added into the ethyl acetate solution and the solvent was removed under reduced pressure. Coated silica gel powder was added to the silica gel column and chromatographed. The eluant was ethyl acetate/n-hexane (7/3). The white platelet crystal thus obtained was further recrystallized with ethyl acetate/n-hexane mixture. The melting point of the product was 60° C.
Spectral Data: IR: cm$^{-1}$ 1725 (C=O) Mass spectrum, m/e (relative intensity) 310 (M$^+$, 37) 251 (M$^+$—CH$_3$CO$_2$, 100) 192 (M$^+$—2CH$_3$CO$_2$, 34)

EXAMPLE 31

Synthesis of 5-(hydroxymethyl-5'-formyl-2,2'-bithiophene (NSC code #647073)

Phosphorus oxychloride ("POCl$_3$") (1 ml) was added into dimethyl formamide (20 ml) slowly under nitrogen gas atmosphere in ice bath and stirred for 1 hour. The dimethyl formamide solution (5 ml) of 5-hydroxymethyl-2,2'-bithiophene (0.5 g) was dropped in slowly. The mixture was stirred for half an hour at room temperature, then the temperature was raised to 50° C. and was further stirred for 3 hours. The reaction solution was poured into potassium carbonate ice water solution. Then the solution was extracted with 100 ml of ethyl acetate. The extract was washed with water and dried over anhydrous magnesium sulfate. The solvent was removed under reduced pressure, and the residual solid was purified by column chromatography, eluted with ethyl acetate/n-hexane (3/7). Light yellowish product was recrystallized from ethyl acetate/n-hexane mixture. The melting point of the product was 123°–124° C. The yield was 85%.
Spectral Data:
$^1$H NMR 400 MHz (CDCl$_3$), δ value 9.91 (s, 1H, —CHO), 7.73–7.02 (m, 4H, protons of thiophene) 4.91–4.90 (d, 2H, —CH$_2$OH) IR (KBr): cm$^{-1}$ 3300 (OH), 1640 (C=O) Mass spectrum, m/e (relative intensity) 224 (M$^+$, 100), 207 (M$^+$—OH, 57), 195 (M$^+$—OH— —CHO, 22)

Preparation of 5-hydroxymethyl-2,2'-bithiophene

To a solution of 5-formyl-2,2'-bithiophene (20 g) in methanol (50 ml) was added sodium borohydride. The reaction mixture was stirred at room temperature and monitored with thin layer chromatography until the reaction completed. After removal of methanol, water was added to dissolve inorganic salts and extracted with dichloromethane. The extract was washed with brine, dried over anhydrous magnesium sulfate, concentrated to give product (20.1 g, 99%), melting point 52°–53° C.
Spectral Data:
$^1$H NMR (DMSO-D$_6$), δ value 7.4–6.6 (m, 5H), 5.51 (t, 2H), 4.5 (d, 2H) UV$_{max}$: 320–300 nm IR: cm$^{-1}$ 3250 (O—H) Mass spectrum: m/e 196 (M$^+$)

EXAMPLE 32

Synthesis of 5-acetoxymethyl-5'-formyl-2,2'-bithiophene (NSC code #647453)

5-Hydroxymethyl-5'-formyl-2,2'-bithiophene (0.2 g) and pyridine (1 ml) were mixed together. Acetic anhydride (1 ml) was added slowly into the mixture with stirring. Ethyl acetate (200 ml) and water (50 ml) were added 2 hours later. The ethyl acetate layer was washed with weak base, weak acid and water. The product was concentrated and purified by column chromatography, eluted with ethyl acetate/n-hexane (1/9). Light yellowish crystals were obtained. The melting point of the crystal was 89°–91° C. The yield was 95%.

Spectral Data:

$^1$H NMR 400 MHz (CDCl$_3$), δ value 9.83 (s, 1H, —CHO), 7.64–7.01 (m, 4H, protons of thiophene) 5.20 (s, 2H, —CH$_2$OAc), 2.08 (s, 3H, —COCH$_3$) IR (KBr): cm$^{-1}$ 1740, 1660 (C═O)

EXAMPLE 33

Synthesis of 5-hydroxymethyl-5"-formyl-α-terthiophene (NSC code #647455)

POCl$_3$ (1 ml) was added to dimethyl formamide (30 ml) slowly under nitrogen stream in ice bath. The solution was stirred for 0.5 hour and then dimethyl formamide solution (20 ml) of 5-hydroxymethyl-α-terthiophene (0.3 g) was dropped in slowly. The mixture was stirred for an hour at room temperature and then the temperature was raised to 60° C. and stirred for 2 more hours. The reaction solution was poured into ice aqueous potassium carbonate solution. The solution was extracted with 300 ml of ethyl acetate and the extract was washed with water. The solvent was removed under reduced pressure and the residual solid was purified by column chromatography, eluted with ethyl acetate/n-hexane (3/7). Orange crystals were obtained and the melting point of the product was 176°–177° C. The yield was 80%.

Spectral Data:

$^1$H NMR (CDCl$_3$), δ value 9.86 (s, 1H, —CHO), 7.65–6.91 (m, 6H, protons of thiophene) 4.80 (s, 2H, —CH$_2$OH) IR (KBr): cm$^{-1}$ 3400 (OH), 1660 (C═O) Mass spectrum, m/e (relative intensity) 306 (M$^+$, 100), 289 (M$^+$, —OH 56)

Preparation of 5-hydroxymethyl-α-terthiophene

To a solution of 5-formyl-α-bithiophene (0.5 g) in tetrahydrofuran (20 ml) was added sodium borohydride (0.034 g). The reaction mixture was stirred at room temperature for 2 hours and monitored with thin layer chromatography until the reaction completed. Water (50 ml) was added slowly and extracted with chloroform. The extract was dried over anhydrous magnesium sulfate, concentrated to give yellowish powder, melting point 151°–152° C., yield 97%.

Spectral Data:

$^1$H NMR (DMSO-d$_6$), δ value 7.51 (d, 1H, J=4 Hz), 7.31 (dd, 1H, J$_1$=1, 4 Hz), 7.24 (d, 1H, J=4 Hz), 7.20 (d, 1H, J=4 Hz), 7.15 (d, 1H, J=4 Hz), 7.09 (dd, 1H, J=3.5, 4 Hz), 6.91 (d, 1H, J=4 Hz), 5.52 (d, 1H, J=6 Hz), 4.60 (d, 2H, J=6 Hz) UV$_{max}$: λ$_{max}$: 355 nm IR (KBr): cm$^{-1}$ 3300 (O—H), 3061 (═C—H), 2950 (—C—H), 1060 (C—O) Mass spectrum: m/e #278 (M$^+$)

EXAMPLE 34

Synthesis of 5,5"-dihydroxymethyl -α-terthiophene (NSC code #646270)

5,5"-Diformyl-α-terthiophene (1 g) was added into tetrahydrofuran (150 ml). The temperature was raised to 50° C. until the solid was completely dissolved, then NaBH$_4$ (0.25 g) was added and stirred for 3 hours at 50° C. The solvent was removed under reduced pressure. Ethyl acetate and water were added to dissolve the residual solid. The ethyl acetate layer was washed with water and dried over anhydrous magnesium sulfate. The ethyl acetate layer was filtered and concentrated to obtain light yellowish crystals (0.95 g) and the melting point of the product was 182°–183° C.

Spectral Data:

$^1$H NMR 400 MHz (CDCl$_3$), δ value 7.04–6.89 (m, 6H, protons of thiophene) 4.79 (d, 4H, CH$_2$OH), 1.51 (br. s., OH) Mass spectrum, m/e (relative intensity) 308 (M$^+$, 58), 306 (M$^+$—2H, 100)

EXAMPLE 35

Synthesis of 5-hydroxymethyl-5"-(1-hydroxypropyl)-α-terthiophene (1) POCl$_3$ (0.5 ml) was added to dimethyl formamide (30 ml) slowly under nitrogen stream in ice bath condition. The solution was stirred for 1 hour and dimethyl formamide solution (200 ml) of 5-hydroxymethyl-α-terthiophene (0.8 g) was dropped in slowly. Then heated to 70° C. with oil bath for 3 hours. The reaction solution was thus placed into 50 ml of aqueous K$_2$CO$_3$ solution at 0° C. The solution was extracted with 500 ml of ethyl acetate. The residual solid was purified by column chromatography, diluted with ethyl acetate/n-hexane (3/7). After removal of solvent, the residue was dissolved in 50 ml of tetrahydrofuran under nitrogen stream and dropped in 1 ml of Ethyl Grignard reagent and stirred at room temperature for 3 hours. The solution was monitored by thin layer chromatography. After the reaction was completed, then the solution was extracted with 300 ml of ethyl acetate and 50 ml of water. After removal of solvent, the residual solid was purified by column chromatography, eluted with ethyl acetate/n-hexane (3/7). Orange powder was thus obtained and the melting point of the product was 131° C.

(2) 5-Hydroxymethyl-5"-formyl-α-terthiophene (0.5 g) was dissolved into anhydrous tetrahydrofuran (50 ml). A slightly excessive amount of ethyl magnesium bromide (2.0 M) was added to the solution under nitrogen atmosphere. The solution was stirred for 3 hours at room temperature. Aqueous ammonium chloride solution was added to hydrolyze the above reaction solution to obtain the crude product. The crude product was collected and purified by column chromatography, eluted with ethyl acetate/n-hexane (3/7). The eluate was concentrated to obtain orange powder (0.3 g). The melting point was 131°–132° C.

Spectral Data:

$^1$H NMR (CDCl$_3$), δ value 7.03–6.85 (m, 6H, protons of thiophene) 4.79–4.78 (m, 3H, —CH$_2$OH and —CHC$_2$H$_5$) 1.91–1.77 (m, 2H, —CH$_2$CH$_3$), 0.99–0.95 (t, 3H, —CH$_3$) IR (KBr): cm$^{-1}$ 3400 (OH), 2900 (saturated CH)

EXAMPLE 36

Synthesis of 5-succinoylmethyl-2,2'-bithiophene

5-Hydroxymethyl-2,2'-bithiophene (2.5 g), pyridine (20 ml) and succinic anhydride (1.2 g) were mixed together and stirred at 40° C. Thin layer chromatography was applied to monitor the reaction. After the reaction was completed, ethyl acetate and diluted hydrochloric acid were added. The reaction solution was concentrated and then mixed with n-hexane for crystallization. White crystals (2.43 g) were then obtained and melting point thereof was 112° C.

Spectral Data:

$^1$H NMR (CDCl$_3$): δ value 7.20–6.90 (m, 5H, protons of thiophene), 5.23 (s, 2H, —CH$_2$O—) 2.69–2.61 (m, 4H, —COCH$_2$CH$_2$CO—), 2.40 (br, OH) IR (KBr): cm$^{-1}$ 3200–2500 (OH) 1720, 1690 (C=O)

EXAMPLE 37

Synthesis of 5,5'-disuccinoylmethyl-2,2'-bithiophene 5,5'-Dihydroxymethyl-2,2'-bithiophene (0.5 g), pyridine (10 ml) and succinic anhydride (2 g) were mixed together. The mixture was stirred at 40° C. Thin layer chromatography was applied to monitor the reaction. After the reaction was completed, ethyl acetate was added to extract the product. The ethyl acetate layer was washed with diluted hydrochloric acid and water in order to remove pyridine completely. The product was filtered through silica gel and recrystallized from ethyl acetate/n-hexane. White crystals (0.45 g) were obtained. The melting point of the crystal was 137° C.

Spectral Data:

1H NMR (CDCl$_3$), δ value 7.00–6.90 (m, 4H, protons of thiophene), 5.28–5.23 (m, 4H, —CH$_2$O—) 4.78–4.75 (m, 4H, —CH$_2$O—), 2.69–2.64 (m, 8H, —CO—CH$_2$CH$_2$—CO—) IR (KBr): cm$^{-1}$ 3600–2500 (OH) 1718, 1688 (C=O)

EXAMPLE 38

Synthesis of 5-succinoylmethyl-5'-formyl-2,2'-bithiophene

5-Hydroxymethyl-5'-formyl-2,2'-bithiophene (0.63 g), pyridine (10 ml) and succinyl anhydride (0.12 g) were mixed together. The mixture was stirred at 40° C. Thin layer chromatography was applied to monitor the reaction. After the reaction was completed, diluted hydrochloric acid and ethyl acetate were added. The ethyl acetate solution was washed with water to remove pyridine completely. Then the ethyl acetate layer was dehydrated with anhydrous magnesium sulfate and filtered through silica gel layer. After removal of the solvent, the product was recrystallized from ethyl acetate/n-hexane to give a light yellowish crystals (0.6 g). The melting point was 127° C.

Spectral Data:

$^1$H NMR (CDCl$_3$), δ value 9.84 (s, 1H, —CHO), 7.65–7.02 (m, 4H, protons of thiophene ) 5.25 (s, 2H, —CH$_2$O—), 2.72–2.64 (m, 4H, —COCH$_2$CH$_2$CO—) 2.40 (br, OH) IR (KBr): cm$^{-1}$ 3200–2500 (OH) 1730, 1705, 1650 (C=O)

EXAMPLE 39

Synthesis of 5-formyl-2,2': 5', 3"-terthiophene (NSC code #660643)

In a two-necked round bottomed flask was added 5-dimethoxymethyl-5'-tributyl-stannyl-2,2'-bithiophene (5.6 g), bis(triphenylphosphine)palladium (II) chloride (0.32 g), 3-bromo-thiophene (1.5 g) (Aldrich Chem. Co., Milwaukee, Wis.) and tetrahydrofuran (20 ml). The reaction mixture was refluxed for 16 hours. To the reaction mixture was then added hydrochloric acid (1N, 3 ml) and was further refluxed for 3 hours. Saturated sodium bicarbonate aqueous solution was added to neutrality and extracted with ethyl acetate. The extract was washed with brine, dried over anhydrous magnesium sulfate and concentrated. The residue was separated by silica gel chromatography, eluted with n-hexane/ethyl acetate (9:1 →1:1 gradient) to give brownish solid product (0.7 g, 40%), melting point 155°–157° C.

Spectral Data:

$^1$H NMR (CDCl$_3$), δ value 9.86 (s, 1H), 7.67 (d, 1H, J=3.8 Hz), 7.44–7.23 (m, 5H), 7.15 (d, 1H, J=3.8 Hz) IR (CH$_2$Cl$_2$): cm$^{-1}$ 1695 (C=O) Mass spectrum, m/e (relative intensity) 276 (M$^+$, 100), 270 (12), 247 (8), 203 (24), 127 (6)

Preparation of 5-dimethoxymethyl-5'-tributylstannyl-2,2'-bithiophene

To a solution of 5-dimethoxymethyl-2,2'-bithiophene (1.0 g) in tetrahydrofuran (20 ml) with ice bath cooling was added n-butyllithium (1.6M in hexane, 3.0 ml). The ice bath was removed and the reaction mixture was stirred at room temperature for 1 hour. Then cooled with ice bath again and tributyltin chloride (1.14 ml) was added. The reaction mixture was further stirred at room temperature for 4 hours. Solvent was removed and the residue was quickly filtered through aluminum oxide eluted with n-hexane to give desired product (1.6 g).

Spectral Data:

$^1$H NMR (CDCl$_3$), δ value 7.28–7.26 (m, 1H), 7.06–7.04 (m, 2H), 6.97–6.94 (m, 1H), 5.61 (s, 1H) 3.38 (s, 6H), 1.62–0.87 (m, 27H)

Preparation of 5-dimethoxymethyl-2,2'-bithiophene

Trimethyl orthoformate (7.5 ml) and montmorillonite K-10 (5.0 g) (Aldrich Chem. Co., Milwaukee, Wis.) were mixed and stirred at room temperature for 10 minutes. A solution of 5-formyl-2,2'-bithiophene (5.0 g) (Aldrich Chem. Co., Milwaukee, Wis.) in n-hexane (10 ml) was added and was stirred at room temperature. The reaction was monitored with thin layer chromatography until the reaction was completed. Montmorillonite K-10 was filtered. The filtrate was added to a saturated sodium bicarbonate aqueous solution and extracted with ethyl acetate (15 ml×3). The extract was washed with brine, dried over anhydrous magnesium sulfate and concentrated to give light yellowish oily product (6.4 g).

Spectral Data:

$^1$H NMR (CDCl$_3$), δ value 7.19–7.13 (m, 2H), 7.05 (d, 1H, J=4.0 Hz), 7.00–6.94 (m, 2H), 5.59 (d, 1H, J=0.5 Hz), 3.37 (s, 6H)

EXAMPLE 40

Synthesis of 5-hydroxymethyl-2,2': 5', 3"-terthiophene (NSC code #660644)

To a solution of 5-formyl-2,2':5', 3"-terthiophene (0.5 g) in methanol (15 ml) was added excess amount of sodium borohydride. The reaction mixture was stirred at room temperature for 40 minutes. Methanol was removed and water was added. The solution was extracted with ethyl acetate, washed with brine, dried over anhydrous magnesium sulfate and concentrated to give brownish solid product (0.5 g), melting point 158°–160° C.

Spectral Data:

$^1$H NMR (CDCl$_3$), δ value 7.40–7.27 (m, 3H), 7.11–7.03 (m, 2H), 6.92 (d, 1H, J=3.49 Hz), 4.81 (s, 2H), 1.62 (brs, OH) IR (CHCl$_3$): cm$^{-1}$ 3650(O—H) Mass spectrum, m/e (relative intensity) 278 (M$^+$,100), 261 (55), 245 (9), 216 (8), 203 (15), 127 (5)

EXAMPLE 41

Synthesis of 4-formyl-5-hydroxymethyl-2,2': 5', 2"-terthiophene (NSC code #663562)

In a two-necked round bottomed flask was added 5-tributylstannyl-2,2'-bithiophene (2.04 g), bis (triphenylphosphine)palladium (II) chloride (0.19 g), 3-formyl-2-hydroxymethyl-5-iodo-thiophene (1.0 g) and tetrahydrofuran (20 ml). The reaction mixture was refluxed for 16 hours. Extracted with ethyl acetate, washed with brine, dried over anhydrous magnesium sulfate and concentrated. The residue was separated by silica gel chromatography, eluted with n-hexane/ethyl acetate (9:1→1:1 gradient) to give brownish solid product (0.43 g, 38%), melting point 108°–110° C.
Spectral Data:
$^1$H NMR (CDCl$_3$), δ value 10.01 (s, 1H), 7.56 (s, 1H), 7.45 (dd, 1H, J=1.0, 5.2 Hz ), 7.32 (dd, 1H, J=1.06, 4.7 Hz), 7.25 (q, 2H), 7.09 (dd, 1H, J=5.04, 5.2 Hz), 5.21–5.15 (m, 3H) IR (CH$_2$Cl$_2$): cm$^{-1}$ 3630 (O—H), 1690 (C=O) Mass spectrum, m/e (relative intensity) 306 (M$^+$,100), 277 (22), 249 (29), 216 (21), 171 (13), 127 (13), 108 (10)
Preparation of 3-formyl-2-hydroxymethyl-5-iodothiophene To a solution of 3-dimethoxymethyl-2-formylthiophene (8.8 g) in methanol was added excess amount of sodium borohydride and stirred at room temperature for 2 hours. Methanol was removed and residue was dissolved in ethyl acetate. The solution was washed with water, dried over anhydrous magnesium sulfate and concentrated. The crude intermediate was then dissolved in methanol (40 ml). Iodine (4.5 g) was added and then iodic acid (2.2 g) in water (10 ml) was added dropwisely. The solution mixture was stirred at room temperature for 4 hours. Methanol was removed and sodium thiosulfate (10%) was added to quench the unreacted iodine. Extracted with ethyl acetate, washed with brine, dried over anhydrous magnesium sulfate, concentrated and separated by silica gel chromatography to give yellowish oily product (10.4 g, 70%).
Spectral Data:
$^1$H NMR (CDCl$_3$), δ value 9.87 (s, 1H), 7.61 (s, 1H), 4.98 (s, 2H), 3.49 (s, 1H)
Preparation of 3-dimethoxymethyl-2-formylthiophene To a solution of 3-dimethoxymethylthiophene (14 g) in tetrahydrofuran (80 ml) was slowly added n-butyllithium (1.6M in n-hexane, 47.8 ml) at −10° C. with stirring. The reaction mixture was further stirred at same temperature for 1 hour. N,N-Dimethyl-formamide (11.9 g) in tetrahydrofuran (40 ml) was then added. The reaction mixture was warmed to room temperature and stirred for overnight. Ice water was added and extracted with ethyl acetate. The extract was dried over anhydrous magnesium sulfate and concentrated to give brownish oily product (13 g, 80%).
Spectral Data:
$^1$H NMR (CDCl$_3$), δ value 10.25 (d, 1H, J=1.16 Hz), 7.65 (dd, 1H, J=1.05, 4.03 Hz), 7.24 (d, 1H, J=5.12 Hz), 5.82 (s, 1H), 3.38 (s, 6H)

EXAMPLE 42

Synthesis of 4,5 dihydroxymethyl-2,2': 5',2"-terthiophene (NSC code #663561)

To a solution of 4-formyl-5-hydroxymethyl-2,2':5', 2"-terthiophene (0.1 g) in methanol (10 ml) was added excess amount of sodium borohydride. The reaction mixture was stirred at room temperature for 40 minutes. Methanol was removed and water was added. The solution was extracted with ethyl acetate, washed with brine, dried over anhydrous magnesium sulfate and concentrated to give brownish solid product (0.1 g), melting point 99°–101° C.
Spectral Data:
$^1$H NMR (CDCl$_3$), δ value 7.42 (dd, 1H, J=6.29 Hz), 7.28 (dd, 1H, J=1.13, 3.61 Hz), 7.20–7.13 (m, 3H), 7.07 (dd, 1H, J=4.92, 5.29 Hz), 4.77 (d, 2H, J=5.64 Hz), 4.57 (d, 2H, J=5.70 Hz) 4.28 (t, OH), 3.68 (t, OH) IR (CHCl$_3$): cm$^{-1}$ 3630(O—H) Mass spectrum, m/e (relative intensity) 308 (M$^+$, 100), 291 (34), 262 (24), 261 (23), 217 (18), 216 (12), 171 (10), 127 (11)

EXAMPLE 43

Synthesis of 5-formyl-4"-hydroxymethyl-2,2':5'2"-terthiophene (NSC code #658879)

In a two-necked round bottomed flask was added 5-dimethoxymethyl-5'-tributyl-stannyl-2,2'-bithiophene (2.12 g, 4.0 mole), bis(triphenylphosphine)-palladium (II) chloride (140 mg, 0.2 mmole), 2-iodo-4-hydroxymethylthiophene (0.96 g, 4.0 mmole) [prepared from sodium borohydride reduction of 2-iodo-4-formyl-thiophene (R. Guilard, P. Fournari, and M. Person, Bulletin De La Société Chimique De France, 11, 4121, 1967) in tetrahydrofuran, 95% yield] and tetrahydrofuran (25 ml). The reaction mixture was refluxed for 16 hours. To the reaction mixture was then added hydrochloric acid (1N, 3 ml) and was further refluxed for 3 hours. Saturated sodium bicarbonate aqueous solution was added to neutralize the solution and extracted with ethyl acetate. The extract was washed with brine, dried over anhydrous magnesium sulfate and concentrated. The residue was separated by silica gel chromatography, eluted with n-hexane/ethyl acetate (2:1) to give yellowish solid product (420 mg, 34%), melting point 133°–135° C.
Spectral Data:
$^1$H NMR (CDCl$_3$), δ value 9.86 (s, 1H), 7.67 (d, 1H, J=8 Hz), 7.26–7.22 (m, 3H), 7.16–7.11 (m, 2H), 4.68 (s, 2H) IR (CH$_2$Cl$_2$): cm$^{-1}$ 3620 (O—H), 1680 (C=O) Mass spectrum, m/e (relative intensity) 306 (M$^+$, 100), 233 (9), 69 (8), 28 (15)

EXAMPLE 44

Synthesis of 5,4"-dihydroxymethyl-2,2':5', 2"-terthiophene (NSC code #658878)

To a solution of 5-formyl-4"-hydroxymethyl-2,2':5', 2"-terthiophene (140 mg) in methanol (10 ml) was added sodium borohydride (0.1 g). The reaction mixture was stirred at room temperature for 40 minutes. Methanol was removed and water was added. The solution was extracted with ethyl acetate, washed with brine, dried over anhydrous magnesium sulfate and concentrated to give light yellowish solid product (140 mg), melting point 111°–113° C.
Spectral Data:
$^1$H NMR (CDCl$_3$), δ value 7.18–7.02 (m, 5H), 6.96–6.89 (m, 1H), 5.30 (s, 1H), 4.81 (brs, 2H), 4.67 (s, 3H) IR (CHCl$_3$): cm$^{-1}$ 3650 (O—H) Mass spectrum, m/e (relative intensity) 308 (M$^+$, 100), 292 (14), 291 (60), 275 (10)

EXAMPLE 45

Synthesis of 5-formyl-3"-hydroxymethyl-2,2,':5'2"-terthiophene (NSC code #658876)

In a two-necked round bottomed flask was added 5-dimethoxymethyl-5'-tributyl-stannyl-2,2'-bithiophene (0.77 g), bis(triphenylphosphine)palladium (II) chloride (0.06 g), 3-hydroxymethyl-2-iodothiophene (0.38 g) and tetrahydrofuran (20 ml). The reaction mixture was refluxed for 16 hours. To the reaction mixture was then added hydrochloric acid (1N, 10 ml) and was further refluxed for 3 hours. Saturated sodium bicarbonate aqueous solution was added to neutrality and extracted with ethyl acetate. The extract was washed with brine, dried over anhydrous magnesium sulfate and concentrated. The residue was separated by silica gel chromatography, eluted with n-hexane/ethyl acetate (9:1→1:1 gradient) to give brownish solid product (0.24 g, 50%), melting point 85°–86° C.
Spectral Data:
$^1$H NMR (CDCl$_3$), δ value 9.86 (s, 1H), 7.68 (dd, 1H, J=1.46, 3.96 Hz), 7.32–7.24 (m, 3H), 7.18–7.16 (m, 2H), 4.80 (s, 2H), 1.64 (bs, OH) IR (CH$_2$Cl$_2$): cm$^{-1}$ 3630 (O—H), 1680 (C=O) Mass spectrum, m/e (relative intensity) 306 (M$^+$,100), 289 (23), 273 (13), 227 (11), 203 (11), 171 (18), 121 (15)

Preparation of 3-hydroxymethyl-2-iodothiophene
3-Hydroxymethylthiophene (2.3 g, 20 mmole) (Aldrich Chem. Co., Milwaukee, Wis.) and iodine (2.39 g, 9.4 mmole) were dissolved in ethanol (15 ml). Iodic acid (1.09 g, 6.2 mmole) in water (2 ml) was added dropwisely at 0° C. and was further stirred for 1 hour at the same temperature. The reaction was monitored with thin layer chromatography until the reaction was completed. Sodium thiosulfate aqueous solution was added and extracted with dichloromethane. The extract was washed with brine, dried over anhydrous magnesium sulfate, concentrated and separated by silica gel chromatography, eluted with n-hexane/ethyl acetate (3:1) to give light yellowish oily product (3.9 g, 81%).
Spectral Data:
$^1$H NMR (CDCl$_3$), δ value 7.43 (d, 1H, J=5.2 Hz), 6.96 (d, 1H, J=5.2 Hz), 4.54 (s, 2H)

EXAMPLE 46

Synthesis of 5,3"-dihydroxymethyl 2,2':5',2"-terthiophene (NSC code #658875)

To a solution of 5-formyl-3"-hydroxymethyl-2,2':5',2"-terthiophene (60 mg) in tetrahydrofuran (5 ml) was added sodium borohydride (15 mg). The reaction mixture was stirred at room temperature for 40 minutes. Methanol was removed and water was added. The solution was extracted with ethyl acetate, washed with brine, dried over anhydrous magnesium sulfate and concentrated to give yellowish solid product (60 mg), melting point 93°–95° C.
Spectral Data:
$^1$H NMR (CDCl$_3$), δ value 7.38 (d, 1H, J=5.3 Hz), 7.21–7.13 (m, 3H), 6.92 (d, 1H, J=2.65 Hz), 4.76 (d, 2H, J=6.0 Hz), 4.71 (d, 2H, J=5.53 Hz), 4.59 (t, 1H, J=5.5 Hz, OH), 4.35 (t, 1H, J=5.43 Hz, OH) IR (CHCl$_3$): cm$^{-1}$ 3640 (O—H) Mass spectrum, m/e (relative intensity) 308 (M$^+$, 100) 291 (44) 277 (13) 227 (11) 171 (13), 121 (13)

EXAMPLE 47

The Preparation of Tartaric Acid Salt of Aminomethylterthiophene

To an ethanolic solution (20 mL) containing aminomethylterthiophene (300 mg, 1.08 mmol) was dropwisely added, with stirring, aqueous L-tartaric acid (2.160 mL, 05 M solution prepared from L-tartaric acid (600 mg, 4.0 mmol) in 8 mL of H$_2$O). Ethanol was removed under vacuum and the residue was freeze-dried to give the salt (460 mg).

The Preparation of (2:1) Hydroxypropyl-β-cyclodextrin Complex of the Tartaric Acid Salt of Aminomethylterthiophene To a solution containing hydroxypropyl-β-cyclodextrin (3.60 g) in H$_2$O (50 mL) was added tartaric acid salt of aminomethylterthiophene (460 mg, 1.08 mmol) in one portion and sonicated for 10 minutes. The heterogeneous mixture was heated to near boiling with stirring until a clear solution was resulted. The solution was cooled to room temperature, gravity filtered, and freeze-dried to give (2:1) hydroxypropyl-β-cyclodextrin complex of the tartaric acid salt of aminomethylterthiophene.

The Quantitative calculation of the Amount of Aminomethylterthiophene in (2:1) Hydroxypropyl-β-cyclodextrin Complex of the Tartaric Acid Salt of Aminomethylterthiophene To 25.21 mg of the (2:1) cyclodextrin complex was added 1.10 mg (0.0079 mmol) of nitrophenol and was dissolved in D$_2$O (1 mL) for $^1$H NMR. The ration of aminomethylterthiophene to nitrophenol calculated from the $^1$H NMR integration was 89%. 0.0079 mmol (nitrophenol)×0.89= 0.00704 mmol (aminomethylterthiophene) 0.00704 mmol× 277 g/mol (m.wt. of aminomethylterthiophene)=1.95 mg Since 1.95 mg of aminomethylterthiophene is in 25.21 mg of the cyclodextrin complex, 1.0 mg of aminomethylterthiophene is in 12.93 mg of the cyclodextrin complex.

The solubility of cyclodextrin complex in H$_2$O was tested by dropwisely adding H$_2$O to 30 mg of the cyclodextrin complex, with stirring. The result showed that the 30 mg of the cyclodextrin complex, containing 2.32 mg of aminomethylterthiophene, can be dissolved in 30 μL of H$_2$O to give clear syrup. The result suggests that 1 mL of H$_2$O can dissolve up to 77 mg of aminomethylterthiophene (1000 mg of the cyclodextrin complex) to give clear syrup.

EXAMPLE 48

Other polythiophene compounds prepared in accordance with this invention are those represented by the following structural formulas.

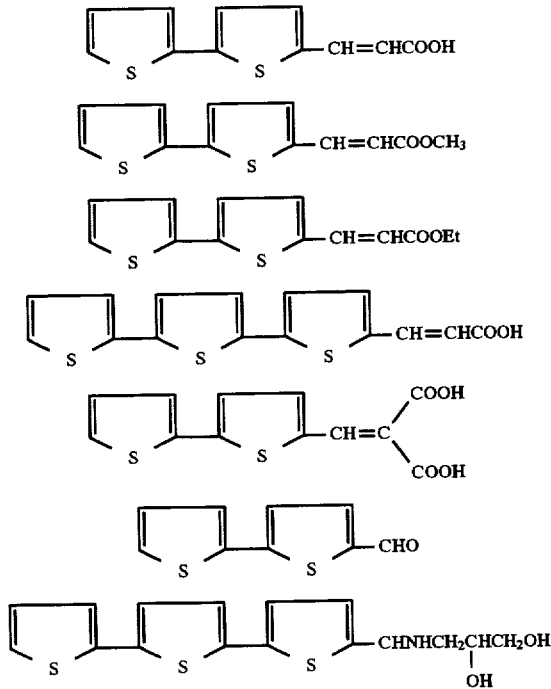

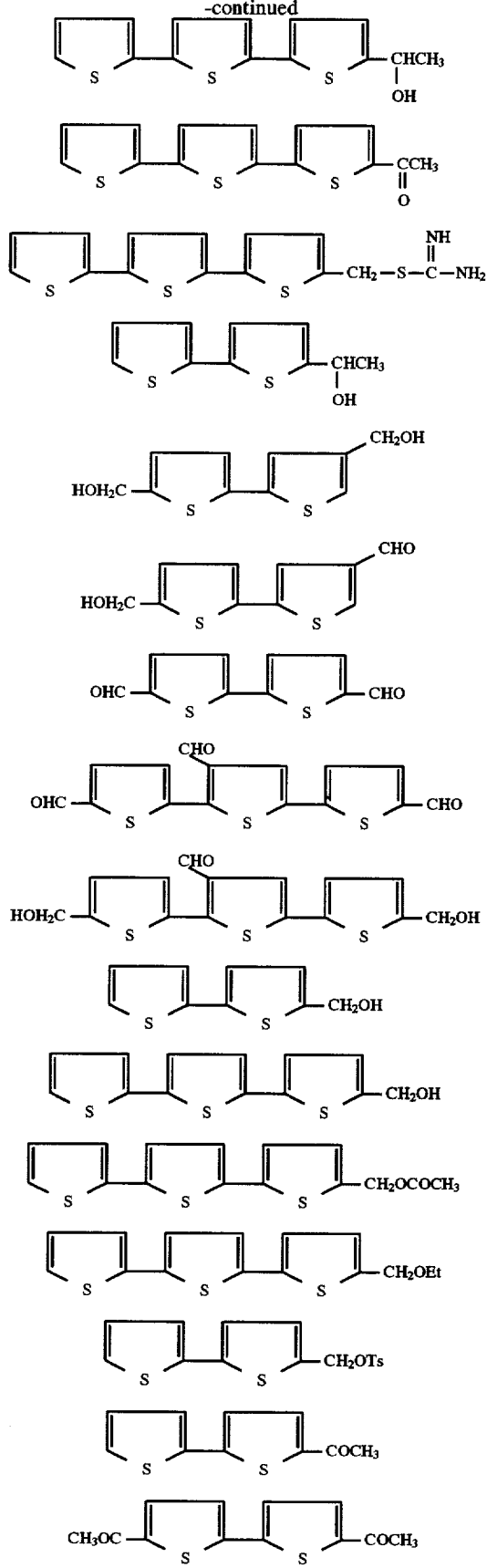
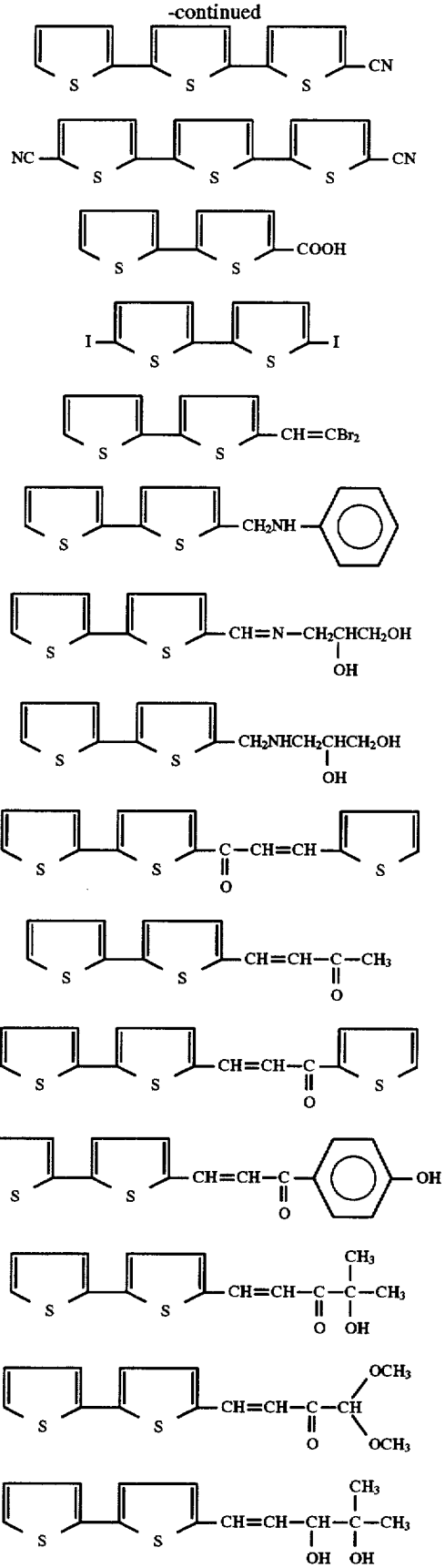

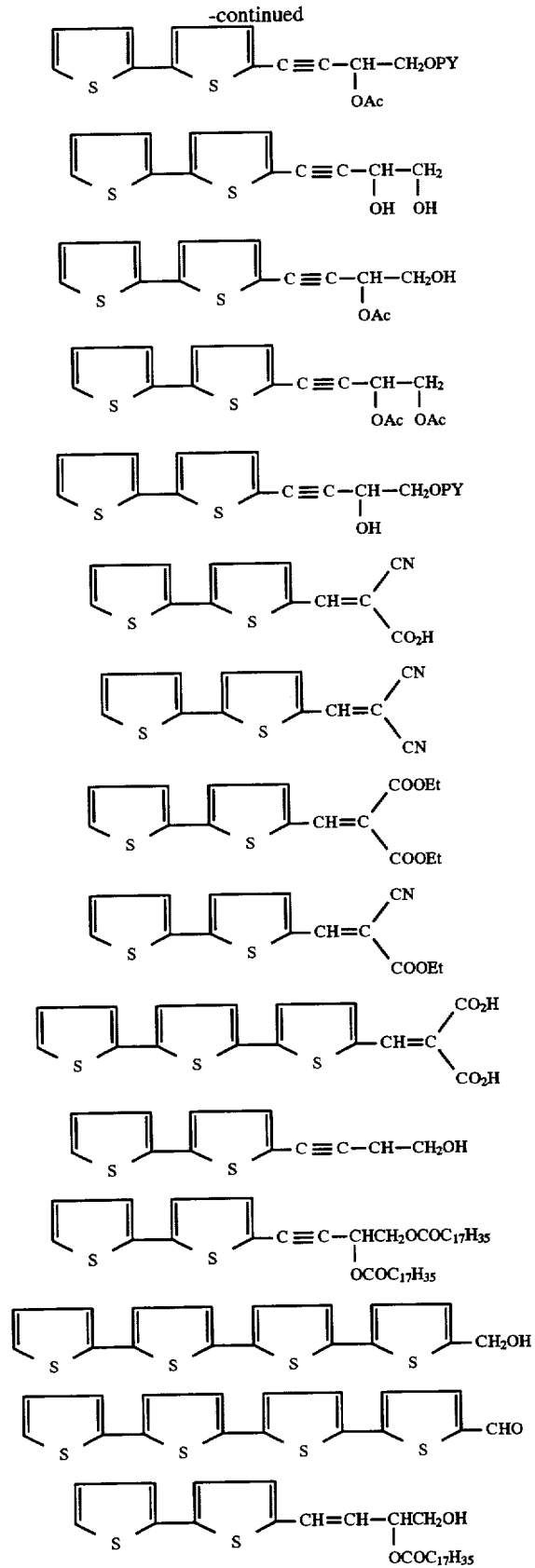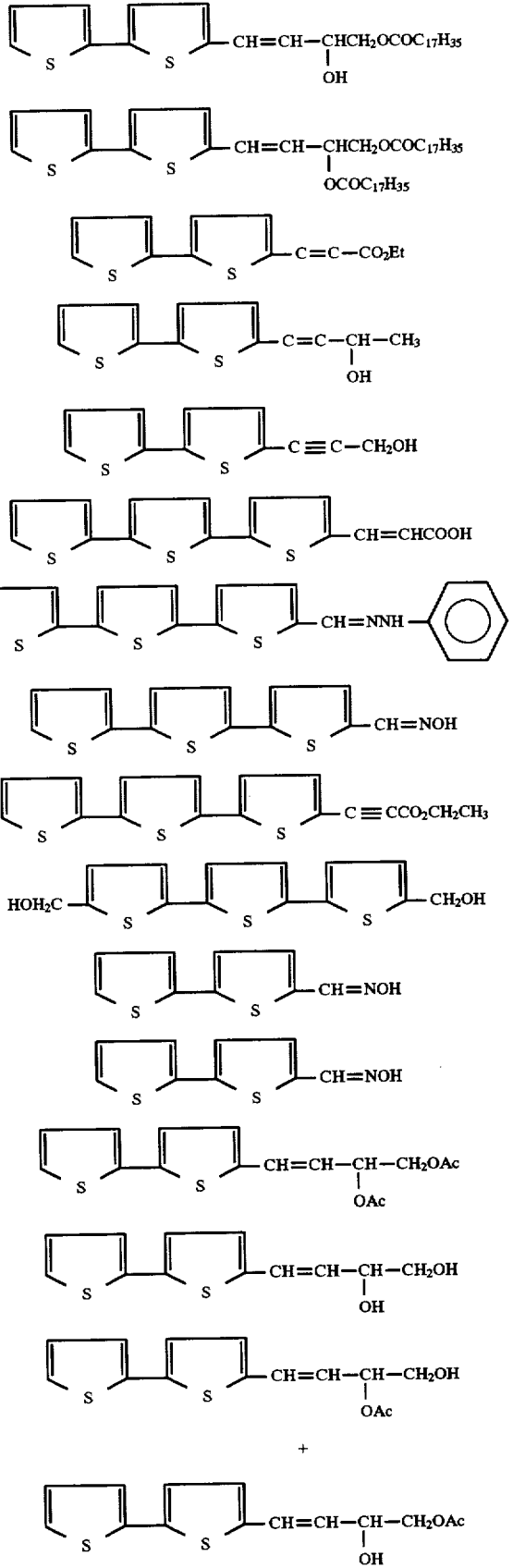

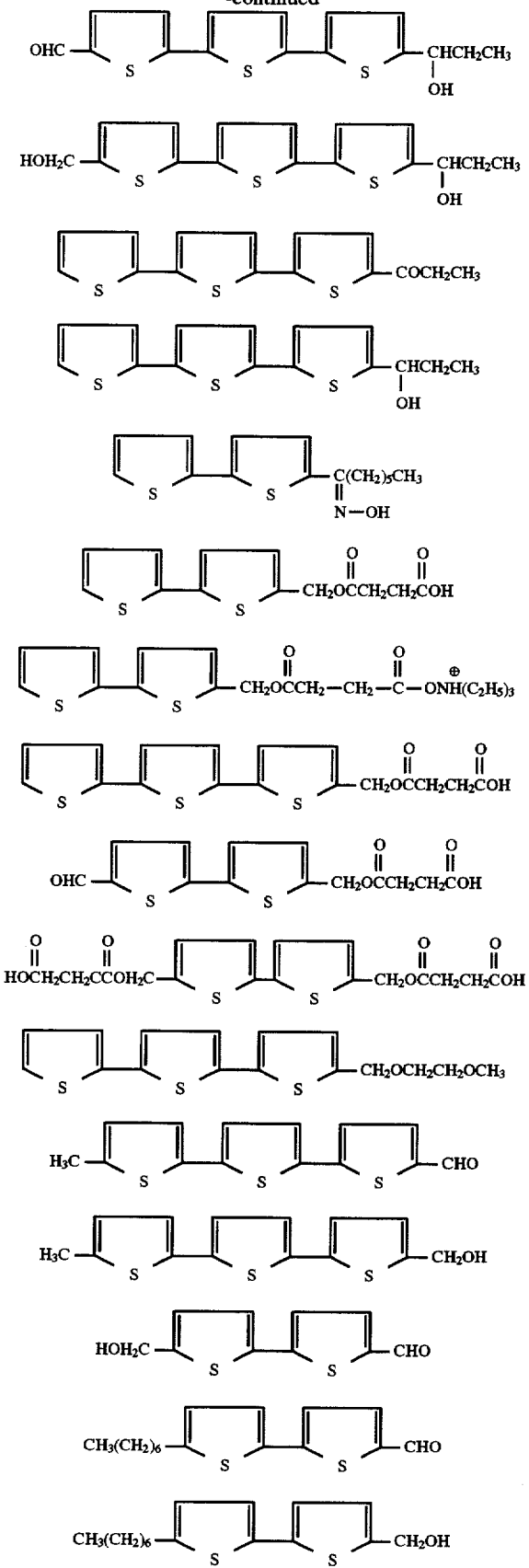
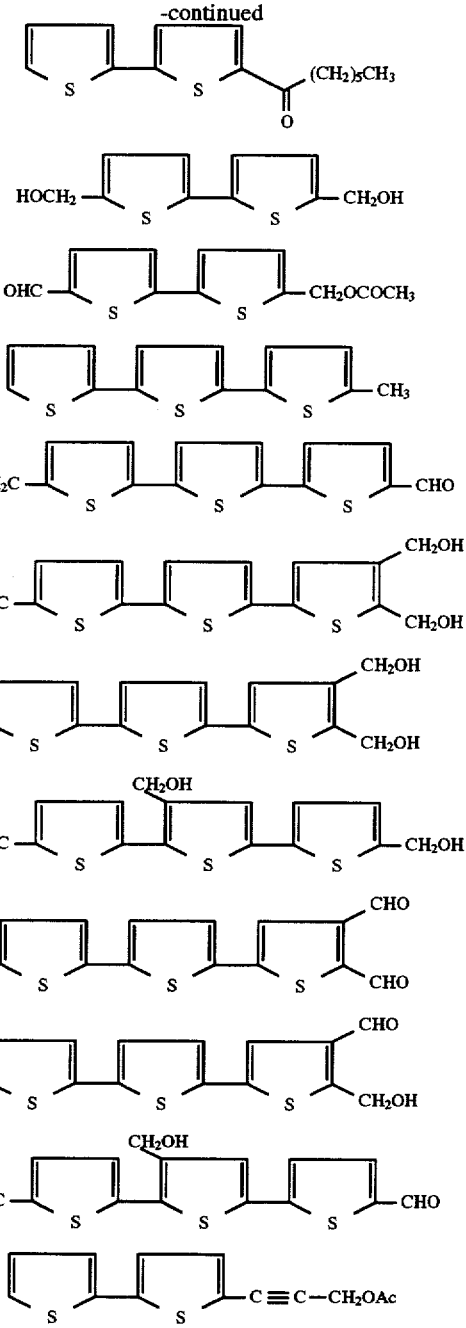

EXAMPLE 49

In Vivo Antitumor Activity

The experiments were carried out at Purdue University athymic mouse laboratory. Athymic mice were purchased from and maintained at the athymic mouse laboratory under pathogenic conditions. Tumor cells (TBE) were obtained from normal human bronchial epithelial cells transfected with plasmic H1 carrying v-Harvey-ras (H-ras) oncogene via protoplast fusion (G. H. Yoakum, J. F. Lechner, E. W. Gabrielson, B. E. Korba, L. Malan-Shibley, J. C. Willey, M. G. Valerio, A. M. Shamsuddin, B. F. Trump and C. C. Harris, Science 227, 1174, 1985. T. C. K. Chan, C.-j. Chang, N. M. Koonchanok and R.L. Geahlen, Biochem. Biophys. Res. Commun., 193, 1152, 1993. The TBE cells were implanted subcutaneously on day 0 of the experiment. Each test group consists of five mice. The compounds tested were dissolved in a saline solution or a saline solution containing 5% of dimethylsulfoxide and 10% cremphor EL (Sigma Chemical Company, St. Louis, Mo.), and were administered intraperitoneously starting on day 2. The solution was administered every four days for a total of four treatments. Tumor volumes were measured every week. The antitumor activity was measured as % of growth inhibition, which is defined by the percentage of the median tumor volume reduction per week of the treated mice divided by the median tumor volume per week of the controlled mice (Tables 9 and 10).

TABLE 9

Antitumor Efficacy of 5-Aminomethyl-α-terthiophene Tartarate-Hydroxypropyl-β-cyclodextrin Complex (NSC Code #660641)
Tumor cells: ras-transformed human bronchial epithelial cells ($2.5 \times 10^6$ cells/mouse)
Formulation: saline solution

| Week | Number of Animals with Tumor | Tumor Volume ($mm^3$) | Slope ($mm^3$/week) | Tumor Growth Inhibition (%) |
|---|---|---|---|---|
| 1. Control | | | | |
| 1 | 1 | 1.3 | | |
| 2 | 1 | 1.3 | | |
| 3 | 3 | 14.7 | 4.41 | |
| 4 | 3 | 16.0 | 4.54 | |
| 5 | 3 | 19.3 | 4.40 | |
| 6 | 3 | 24.3 | 4.41 | |
| 7 | 3 | 34.7 | 4.92 | |
| 8 | 3 | 34.3 | 4.80 | |
| 2. 12 mg/kg | | | | |
| 1 | 0 | 0.0 | | |
| 2 | 0 | 0.0 | | |
| 3 | 1 | 1.2 | 0.36 | 92 |
| 4 | 2 | 4.8 | 1.08 | 76 |
| 5 | 2 | 4.8 | 1.13 | 74 |
| 6 | 2 | 4.8 | 1.03 | 77 |
| 7 | 4 | 8.2 | 1.18 | 76 |
| 8 | 5 | 24.0 | 2.34 | 51 |

*Tumor Growth Inhibition (%) = $\frac{\text{Slope (control)} - \text{Slope (treated)}}{\text{Slope (control)}} \times 100$

TABLE 10

Antitumor Efficacy of 5-Hydroxymethyl-5"-formyl-α-terthiophene (NSC Code #647455)
Tumor cells: ras-transformed human bronchial epithelial cells ($4.0 \times 10^6$ cells/mouse)
Formulation: 5% DMSO and 10% cremphor in saline solution

| Week | Number of Animals with Tumor | Tumor Volume ($mm^3$) | Slope ($mm^3$/week) | Tumor Growth Inhibition (%) |
|---|---|---|---|---|
| 1. Control | | | | |
| 1 | 2 | 2.4 | | |
| 1.5 | 3 | 6.2 | | |
| 2 | 4 | 10.8 | | |
| 3 | 4 | 14.6 | 4.97 | |
| 4 | 4 | 15.8 | 4.37 | |
| 5 | 4 | 15.0 | 3.45 | |
| 6 | 4 | 16.6 | 2.91 | |
| 8.6 | 5 | 23.6 | 2.63 | |
| 2. 25 mg/kg | | | | |
| 1 | 0 | 0.0 | | |
| 1.5 | 1 | 1.4 | | |

TABLE 10-continued

Antitumor Efficacy of 5-Hydroxymethyl-5"-formyl-α-terthiophene (NSC Code #647455)
Tumor cells: ras-transformed human bronchial epithelial cells ($4.0 \times 10^6$ cells/mouse)
Formulation: 5% DMSO and 10% cremphor in saline solution

| Week | Number of Animals with Tumor | Tumor Volume ($mm^3$) | Slope ($mm^3$/week) | Tumor Growth Inhibition (%) |
|---|---|---|---|---|
| 2 | 3 | 5.2 | | |
| 3 | 4 | 5.8 | 2.16 | 57 |
| 4 | 4 | 5.6 | 1.75 | 60 |
| 5 | 4 | 5.4 | 1.34 | 61 |
| 6 | 5 | 10.6 | 1.60 | 45 |
| 8.6 | 5 | 18.8 | 2.07 | 21 |

*Tumor Growth Inhibition (%) = $\frac{\text{Slope (control)} - \text{Slope (treated)}}{\text{Slope (control)}} \times 100$

We claim:
1. A compound of the formula:

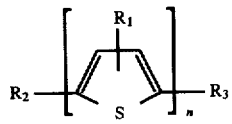

wherein n is 0 or 1, $R_1$ is H, $CH_2OH$, CHO, $CH_2NH_2$.

$R_2$ and $R_3$ are independently selected from the group consisting of mono- or di-substituted 2-thienyl, and mono- or di-substituted 3-thienyl, wherein the thienyl substituents are selected from the group consisting of cyano, $C_1$–$C_7$ haloalkyl, $C_1$–$C_7$ haloalkenyl, $C_1$–$C_4$ alkanoyloxy methyl, $CH_2OR_4$, $COR_5$, $CH_2NR_6R_7$, $CH=CR_9R_{10}$, $CH=NR_{11}$, $CH_2SC(NH)NH_2$ and $C\equiv CR_{12}$ wherein $R_4$ is H, $CO(CH_2)_2CO_2H$, $(CH_2)_2OCH_3$, $C_1$–$C_4$ alkyl or $COC_1$–$C_{17}$ alkyl;

$R_5$ is H or $C_1$–$C_7$ alkyl;

$R_6$ and $R_7$ are independently H, mono- or di-hydroxy$C_2$–$C_4$ alkyl;

$R_8$ is $C_1$–$C_7$ alkyl, or $C_1$–$C_7$ alkenyl;

$R_9$ and $R_{10}$ are independently H, $C_1$–$C_7$ alkyl, $COOR_5$, $CH(OR_4)$ $COOR_5$, Br, CO-thienyl, or $COC_6H_4OH$ (p);

$R_{11}$ is $NHR_4$ or $OR_5$;

$R_{12}$ is $COOR_5$, CH ($OR_5$) $CH_2OR_5$ or CH ($OCOC_1$–$C_4$ alkyl) $CH_2OR_5$; cyclodextrin complexes of such compound; and when $R_2$ or $R_3$ is thienyl substituted with $CH_2NR_6R_7$, the pharmaceutically acceptable salt of the compound represented thereby; with the proviso, that when $R_1$ is H, $R_2$ is selected from the group consisting of di-substituted 2-thienyl, hydroxymethyl- or aminomethyl-substituted 2-thienyl, 3-formyl-2-thienyl and mono- or di-substituted 3-thienyl, and $R_3$ is selected from the group consisting of di-substituted 2-thienyl, hydroxymethyl- or aminomethyl-substituted 2-thienyl, mono- or di-substituted 3-thienyl and formyl substituted 2-thienyl.

2. The compound of claim 1, wherein n=1, $R_1$ is H, $R_2$ is substituted 3-thienyl and $R_3$ is substituted 2-thienyl.

3. The compound of claim 2 wherein $R_3$ is substituted 2-thienyl wherein the substituents are selected from the group consisting of $CH_2NH_2$—$CH_2OH$ and —CHO.

4. The compound of claim 1, wherein n=1, $R_1$ is hydrogen, and $R_2$ is hydroxymethyl 2-thienyl and $R_3$ is substituted 2-thienyl wherein the substituents are selected from the group consisting of $CH_2NH_2$, $CH_2OH$ and —CHO.

5. The compound of claim 1 wherein n=0.

6. The compound of claim 1 wherein $R_2$ is substituted 2-thienyl and $R_3$ is 3- or 4-substituted-2-thienyl wherein the substituents are selected from the group consisting of $CH_2OH$, CHO and $CH_2NH_2$.

7. A compound of the formula:

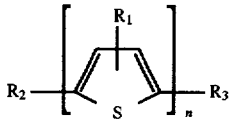

wherein n is 0 or 1, $R_1$ is H, $CH_2OH$, CHO, $CH_2NH_2$, $R_2$ is selected from the group consisting of mono- or di-substituted 2-thienyl, and mono- or di-substituted 3-thienyl, and $R_3$ is selected from the group consisting of 3-thienyl, mono- or di-substituted 3-thienyl, and di-substituted 2-thienyl, wherein the thienyl substituents are selected from the group consisting of cyano, $C_1$–$C_7$ haloalkyl, $C_1$–$C_7$ haloalkenyl, $C_1$–$C_4$ alkanoyloxy methyl, $CH_2OR_4$, $COR_5$, $CH_2NR_6R_7$, CH=$CR_9R_{10}$, CH=$NR_{11}$, $CH_2SC(NH)NH_2$ and C≡$CR_{12}$ wherein $R_4$ is H, $CO(CH_2)_2CO_2H$, $(CH_2)_2OCH_3$, or $COC_1$–$C_{17}$ alkyl;

$R_5$ is H or $C_1$–$C_7$ alkyl;

$R_6$ and $R_7$ are independently H, $C_1$–$C_4$ alkyl, or mono- or di-hydroxy$C_2$–$C_4$ alkyl;

$R_8$ is $C_1$–$C_7$ alkyl, or $C_1$–$C_7$ alkenyl;

$R_9$ and $R_{10}$ are independently H, $C_1$–$C_7$ alkyl, $COOR_5$, $CH(OR_4)COOR_5$, Br, CO-thienyl, or $COC_6H_4OH(p)$;

$R_{11}$ is $NHR_4$ or $OR_5$;

$R_{12}$ is $COOR_5$, $CH(OR_5)CH_2OR_5$ or $CH(OCOC_1$–$C_4$ alkyl)$CH_2OR_5$; cyclodextrin complexes of such compound and when $R_2$ or $R_3$ is thienyl substituted with $CH_2NR_6R_7$, the pharmaceutically acceptable salt of the compound represented thereby.

8. A composition comprising an anti-tumor effective amount of a compound of the formula:

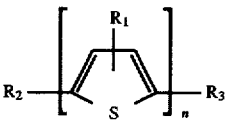

wherein n is 0 or 1, $R_1$ is H, $CH_2OH$, CHO, $CH_2NH_2$, $R_2$ and $R_3$ are independently selected from the group consisting of mono- or di-substituted 2-thienyl, and mono- or di-substituted 3-thienyl, wherein the thienyl substituents are selected from the group consisting of cyano, $C_1$–$C_7$ haloalkyl, $C_1$–$C_7$ haloalkenyl, $C_1$–$C_4$ alkanoyloxy methyl, $CH_2OR_4$, $COR_5$, $CH_2NR_6R_7$, CH=$CR_9R_{10}$, CH=$NR_{11}$, $CH_2SC(NH)NH_2$ and C≡$CR_{12}$ wherein $R_4$ is H, $CO(CH_2)_2CO_2H$, $(CH_2)_2OCH_3$, or $COC_1$–$C_{17}$ alkyl;

$R_5$ is H or $C_1$–$C_7$ alkyl;

$R_6$ and $R_7$ are independently H, $C_1$–$C_4$ alkyl, or mono- or di-hydroxy$C_2$–$C_4$ alkyl;

$R_8$ is $C_1$–$C_7$ alkyl, or $C_1$–$C_7$ alkenyl;

$R_9$ and $R_{10}$ are independently H, $C_1$–$C_7$ alkyl, $COOR_5$, $CH(OR_4)COOR_5$, Br, CO-thienyl, or $COC_6H_4OH(p)$;

$R_{11}$ is $NHR_4$ or $OR_5$;

$R_{12}$ is $COOR_5$, $CH(OR_5)CH_2OR_5$ or $CH(OCOC_1$–$C_4$ alkyl)$CH_2OR_5$; cyclodextrin complexes of such compound and when $R_2$ or $R_3$ is thienyl substituted with $CH_2NR_6R_7$, the pharmaceutically acceptable salt of the compound represented thereby; with the proviso, that when $R_1$ is H, $R_2$ is selected from the group consisting of mono- or di-substituted 2-thienyl, and mono- or di-substituted 3-thienyl, and $R_3$ is selected from the group consisting of mono- or di-substituted 2-thienyl, and mono- or di-substituted 3-thienyl and a pharmaceutically acceptable carrier.

9. The composition of claim 8 wherein n=1, $R_1$ is H, $R_2$ is substituted 3-thienyl and $R_3$ is substituted 2-thienyl.

10. The composition of claim 8 wherein $R_3$ is substituted 2-thienyl wherein the substituents are selected from the group consisting of $CH_2NH_2$, —$CH_2OH$ and —CHO.

11. The composition of claim 8 wherein n=1, $R_1$ is hydrogen, and $R_2$ is hydroxymethyl 2-thienyl and $R_3$ is substituted 2-thienyl wherein the substituents are selected from the group consisting of $CH_2NH_2$, $CH_2OH$ and —CHO.

12. The composition of claim 8 wherein n=0.

13. The composition of claim 8 wherein $R_2$ is substituted 2-thienyl and $R_3$ is 3- or 4-substituted-2-thienyl thienyl wherein the substituents are selected from the group consisting of $CH_2OH$, CHO and $CH_2NH_2$.

14. A method of treating a patient having a tumor, said method comprising the step of administering to the patient an effective amount of a compound of the formula:

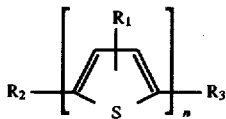

wherein n is 0, or 1, $R_1$ is H, $CH_2OH$, CHO, $CH_2NH_2$, $R_2$ and $R_3$ are independently selected from the group, consisting of 2-thienyl, 3-thienyl, mono- or di-substituted 2-thienyl, or mono- or di- substituted 3-thienyl, wherein the thienyl substituents are selected from the group consisting of cyano, chloro, bromo, iodo, $C_1$–$C_7$ alkyl or haloalkyl, $C_1$–$C_7$ alkenyl or haloalkenyl, $C_1$–$C_4$ alkanoyloxy methyl, $CH_2OR_4$, $COR_5$, $CH_2NR_6R_7$, $CH(OR_4)R_8$, CH=$CR_9R_{10}$, CH=$NR_{11}$, $CH_2SC(NH)NH_2$ and C≡$CR_{12}$ wherein, $R_4$ is H, $CO(CH_2)_2CO_2H$, $(CH_2)_2OCH_3$, $C_1$–$C_4$ alkyl or $COC_1$–$C_{17}$ alkyl;

$R_5$ is H or $C_1$–$C_7$ alkyl;

$R_6$ and $R_7$ are independently H, $C_1$–$C_4$ alkyl, or mono- or di- hydroxy$C_2$–$C_4$ alkyl;

$R_8$ is $C_1$–$C_7$ alkyl, or $C_1$–$C_7$ alkenyl;

$R_9$ and $R_{10}$ are independently H, $C_1$–$C_7$ alkyl, $COOR_5$, $CH(OR_4)COOR_5$, Br, CO-thienyl, or $COC_6H_4OH(p)$;

$R_{11}$ is $NHR_4$ or $OR_5$;

$R_{12}$ is $COOR_5$, $CH(OR_5)CH_2OR_5$ or $CH(OCOC_1$–$C_4$ alkyl)$CH_2OR_5$; cyclodextrin complexes of such compound and when $R_2$ or $R_3$ is thienyl substituted with $CH_2NR_6R_7$, the pharmaceutically acceptable salt of the compound represented thereby; with the proviso, that when $R_1$ is H, $R_2$ is selected from the group consisting of 2-thienyl, 3-thienyl, mono- or di-substituted 2-thienyl, or mono- or di- substituted 3-thienyl, and $R_3$ is selected from the group consisting of 3-thienyl, mono- or di-substituted 2-thienyl, or mono- or di- substituted 3-thienyl.

15. The method of claim 14 wherein n=1, $R_1$ is H, $R_2$ is 3-thienyl or substituted 3-thienyl and $R_3$ is 2-thienyl or substituted 2-thienyl.

16. The method of claim 14 wherein $R_2$ is 3-thienyl and $R_3$ is substituted 2-thienyl wherein the substituents are selected from the group consisting of $CH_2NH_2$—$CH_2OH$ or —CHO.

17. The method of claim 14 wherein n=1, $R_1$ is hydrogen, and $R_2$ is hydroxymethyl 2-thienyl and $R_3$ is substituted 2-thienyl wherein the substituents are selected from the group consisting of $CH_2NH_2$, $CH_2OH$ or —CHO.

18. The method of claim 14 wherein n=0.

19. The method of claim 14 wherein $R_2$ is 2-thienyl or substituted 2-thienyl and $R_3$ is 3- or 4-substituted-2-thienyl wherein the substituents are selected from the group consisting of $CH_2OH$, CHO and $CH_2NH_2$.

* * * * *